United States Patent
Gazit et al.

(10) Patent No.: US 11,554,195 B2
(45) Date of Patent: Jan. 17, 2023

(54) METHOD FOR REGENERATING THE INTERVERTERBRAL DISC WITH NOTOCHORDAL CELLS

(71) Applicant: Cedars-Sinai Medical Center, Los Angeles, CA (US)

(72) Inventors: Zulma Gazit, Los Angeles, CA (US); Dmitriy Sheyn, Los Angeles, CA (US); Gadi Pelled, Los Angeles, CA (US); Dan Gazit, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 386 days.

(21) Appl. No.: 15/739,555

(22) PCT Filed: Jun. 22, 2016

(86) PCT No.: PCT/US2016/038799
§ 371 (c)(1),
(2) Date: Dec. 22, 2017

(87) PCT Pub. No.: WO2016/209987
PCT Pub. Date: Dec. 29, 2016

(65) Prior Publication Data
US 2020/0093961 A1    Mar. 26, 2020

Related U.S. Application Data

(60) Provisional application No. 62/182,816, filed on Jun. 22, 2015.

(51) Int. Cl.
| | |
|---|---|
| *C12N 5/00* | (2006.01) |
| *A61L 27/00* | (2006.01) |
| *A61L 27/38* | (2006.01) |
| *A61L 27/22* | (2006.01) |
| *A61L 27/52* | (2006.01) |
| *C12N 5/077* | (2010.01) |

(52) U.S. Cl.
CPC ......... *A61L 27/3895* (2013.01); *A61L 27/225* (2013.01); *A61L 27/3817* (2013.01); *A61L 27/3878* (2013.01); *A61L 27/52* (2013.01); *C12N 5/0655* (2013.01); *A61L 2300/62* (2013.01); *A61L 2300/64* (2013.01); *A61L 2430/38* (2013.01); *C12N 2501/727* (2013.01); *C12N 2506/45* (2013.01)

(58) Field of Classification Search
CPC . A61L 2430/38; A61L 27/00; C12N 2506/00; C12N 5/00
See application file for complete search history.

(56) References Cited

U.S. PATENT DOCUMENTS

| | | |
|---|---|---|
| 2009/0068270 A1 | 3/2009 | Attawia et al. |
| 2009/0143863 A1 | 6/2009 | Perez-Cruet |
| 2014/0079752 A1 | 3/2014 | Huebsch et al. |

FOREIGN PATENT DOCUMENTS

| | | |
|---|---|---|
| WO | 2007027583 A2 | 3/2007 |
| WO | 2011122601 A1 | 10/2011 |
| WO | 2012112564 A2 | 8/2012 |
| WO | 2016209987 A1 | 12/2016 |

OTHER PUBLICATIONS

Liu et al. "Modulating notochordal differentiation of human induced pluripotent stem cells using natural nucleus pulposus tissue matrix." Plos One, vol. 9,7 e100885 (Jul. 2014) (Year: 2014).*
Nomura et al. "Nucleus Pulposus Allograft Retards Intervertebral Disc Degeneration" Clinical Orthopaedics and Related Research 2001, No. 389, pp. 94-101. (Year: 2001).*
Liu et al. "Native nucleus pulposus tissue matrix promotes notochordal differentiation of human induced pluripotent stem cells with potential for treating intervertebral disc degeneration" J Biomed Mater Res Part A 2015:103A:1053-1059 (published online: Jun. 17, 2014). (Year: 2014).*
Sakai et al. "Future perspectives of cell-based therapy for intervertebral disc disease", EurSpine J (2008) 17 (Suppl 4):S452-S458. (Year: 2008).*
Feng et al. "Transplantation of mesenchymal stem cells and nucleus pulposus cells in a degenerative disc model in rabbits: a comparison of 2 cell types as potential candidates for disc regeneration", J Neurosurg Spine 14:322-329, 2011. (Year: 2011).*
Navaro, Yosi "The effect of matrix elasticity on nucleus pulposusstem cells", Master Thesis, pp. 1-46 (May 2013). (Year: 2013).*
Henriksson et al. "Transplantation of Human Mesenchymal Stems Cells Into Intervertebral Discs in a Xenogeneic Porcine Model", SPINE 2009, vol. 34, No. 2, pp. 141-148. (Year: 2009).*
Pelled et al. "The Effect of Matrix Elasticity On Nucleus Pulposus Stem Cells", Orthopaedic Research Society (ORS) 2014 Annual Meeting, Abstract for Poster No. 1168 (Mar. 2014). (Year: 2014).*
Kirby et al. "Glycogen Synthase Kinase 3 (GSK3) Inhibitor, SB-216763, Promotes Pluripotency in Mouse Embryonic Stem Cells", PLOS ONE (2012), vol. 7, Issue 6, e39329, 13 pages. (Year: 2012).*

(Continued)

*Primary Examiner* — James D Schultz
*Assistant Examiner* — James Joseph Graber
(74) *Attorney, Agent, or Firm* — Linda B. Huber; Nixon Peabody LLP

(57) ABSTRACT

Described herein are compositions and methods related to derivation of human notochordal cells differentiated from induced pluripotent stem cells (iPSCs). The inventors have developed a two-step process for generating these iPSC-derived notochordal cells (iNCs), which can provide a renewable source of therapeutic material for use in degenerative disc disease (DDD). As iNCs are capable of reversing DDD and supporting regeneration of intervertebral disc (IVD) tissue based on the understanding that NC cells maintain homeostasis and repair of other IVD cell types such as nuclear pulposus (NP).

9 Claims, 22 Drawing Sheets
Specification includes a Sequence Listing.

(56) References Cited

OTHER PUBLICATIONS

Bone et al. (2011) "A novel chemically directed route for the generation of definitive endoderm from human embryonic stem cells based on inhibition of GSK-3" Journal of cell science, 124(12), 1992-2000. (Year: 2011).*

Singh et al. (2012) "Signaling network crosstalk in human pluripotent cells: a Smad2/3-regulated switch that controls the balance between self-renewal and differentiation" Cell stem cell, 10(3), 312-326. (Year: 2012).*

Lam et al. (2014) "Rapid and efficient differentiation of human pluripotent stem cells into intermediate mesoderm that forms tubules expressing kidney proximal tubular markers" Journal of the American Society of Nephrology, 25(6), 1211-1225. (Year: 2014).*

Chen et al., Differentiation of Mouse Induced Pluripotent Stem Cells (iPSCs) into Nucleus Pulposus-Like Cells In Vitro, 2013, PLoS One, vol. 8(9).

Erwin et al., Notochordal cells protect nucleus pulposus cells from degradation and apoptosis: implications for the mechanisms of intervertebral disc degeneration, Arthritis Res Ther., 2011, vol. 13(6):R215.

Risbud et al., Defining the Phenotype of Young Healthy Nucleus Pulposus Cells: Recommendations of the Spine Research Interest Group at the 2014 Annual ORS.

Risbud et al., Notochordal Cells in the Adult Intervertebral Disc: New Perspective on an Old Question, 2011, Crit Rev Eukaryot Gene Expr., vol. 21(1):29-41.

Risbud et al., Towards an Understanding of the Role of Notochordal Cells in the Adult Intervertebral Disc: From Discord to Accord, 2010, Dev Dyn., vol. 239(8): 2141-2148.

Liu et al. Modulating Notochordal Differentiation of Human Induced Pluripotent Stem Cells Using Natural Nucleus Pulposus Tissue Matrix, PLoS One, 2014, vol. 9(7), pp. 1-8.

International Search Report and Written Opinion for PCT/US2016/038799 dated Dec. 7, 2016, 11 pages.

Pelled et al. The Effect of Matrix Elasticity on Nucleus Pulposus Stem Cells, ORS 2014 Annual Meeting Poster 1168, Mar. 15, 2014-Mar. 18, 2014.

* cited by examiner

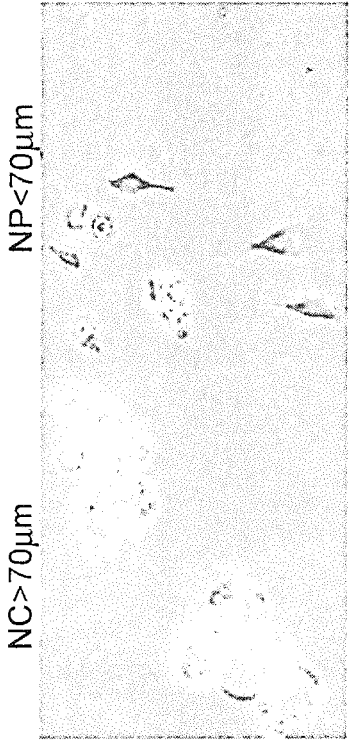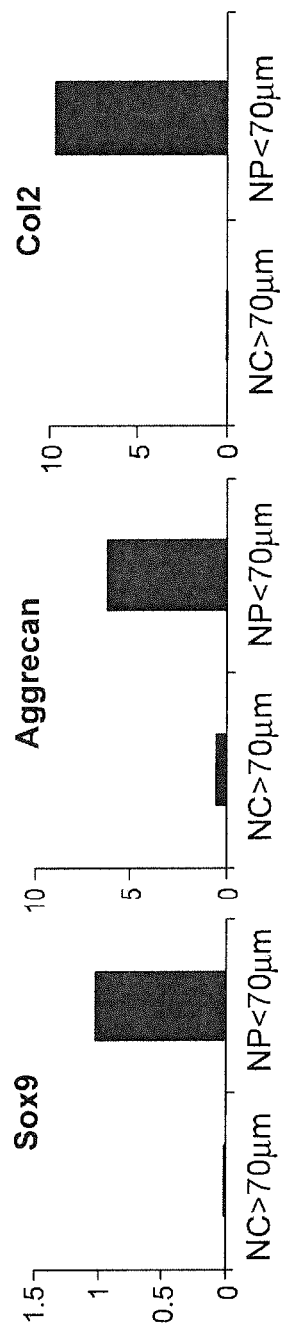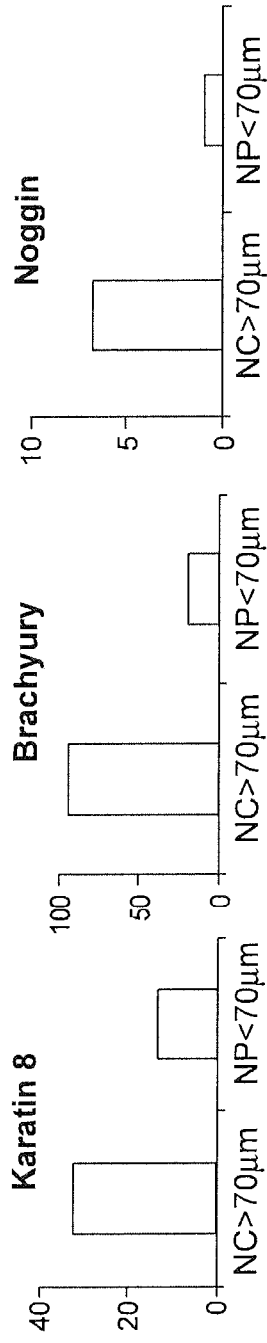

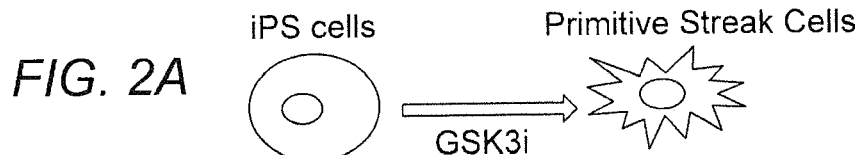
FIG. 2A
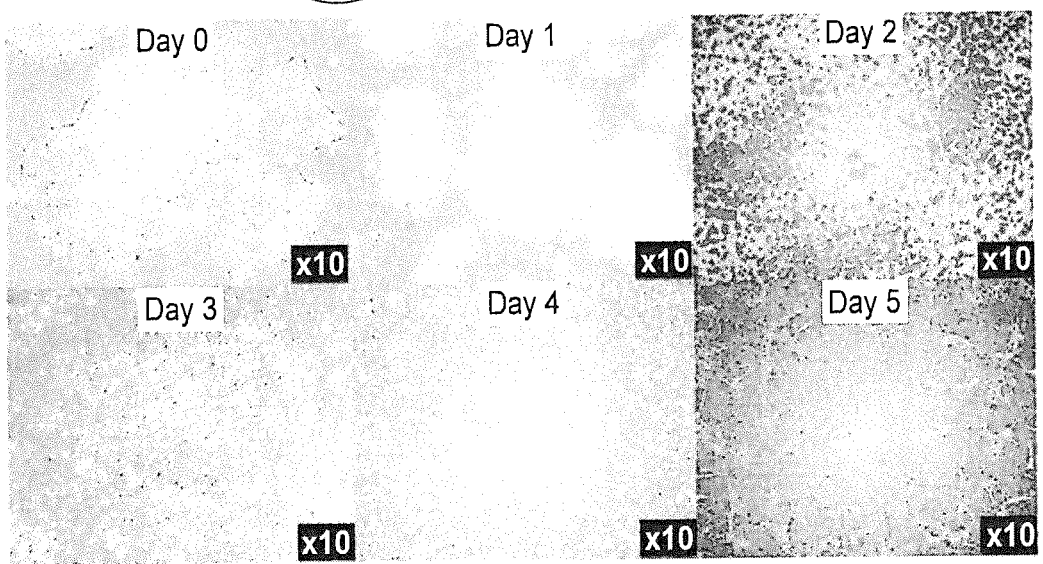
FIG. 2B
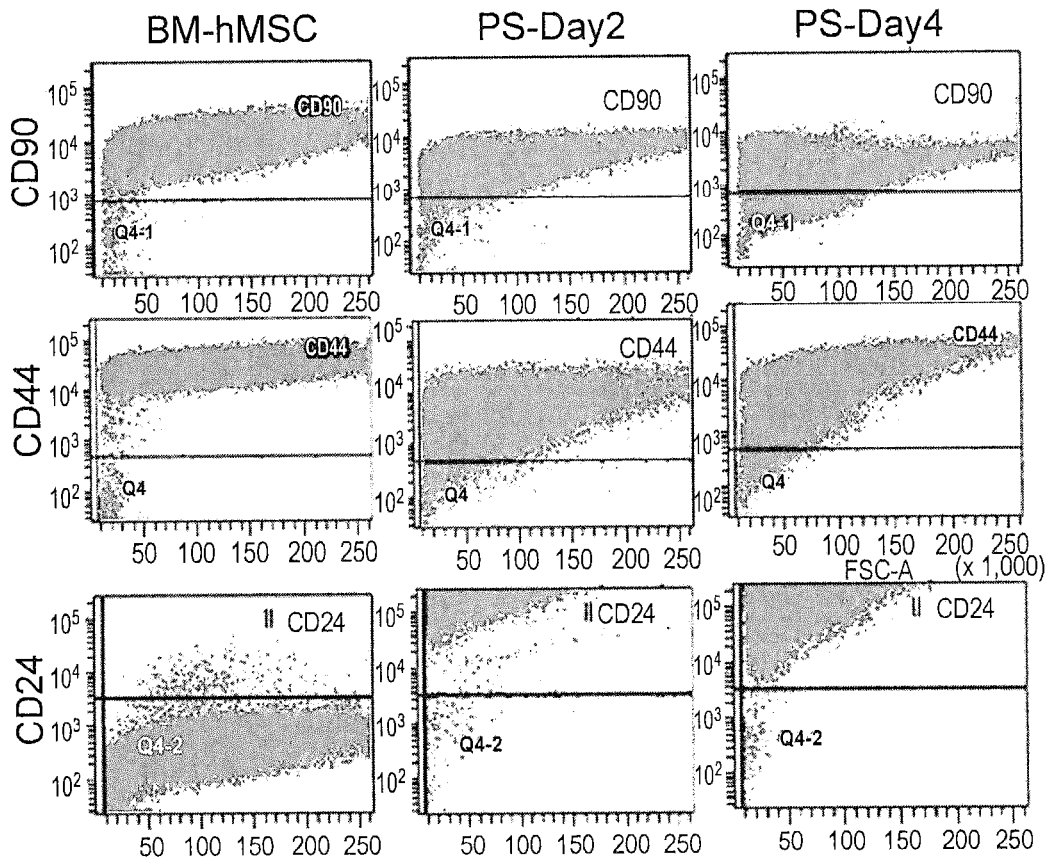

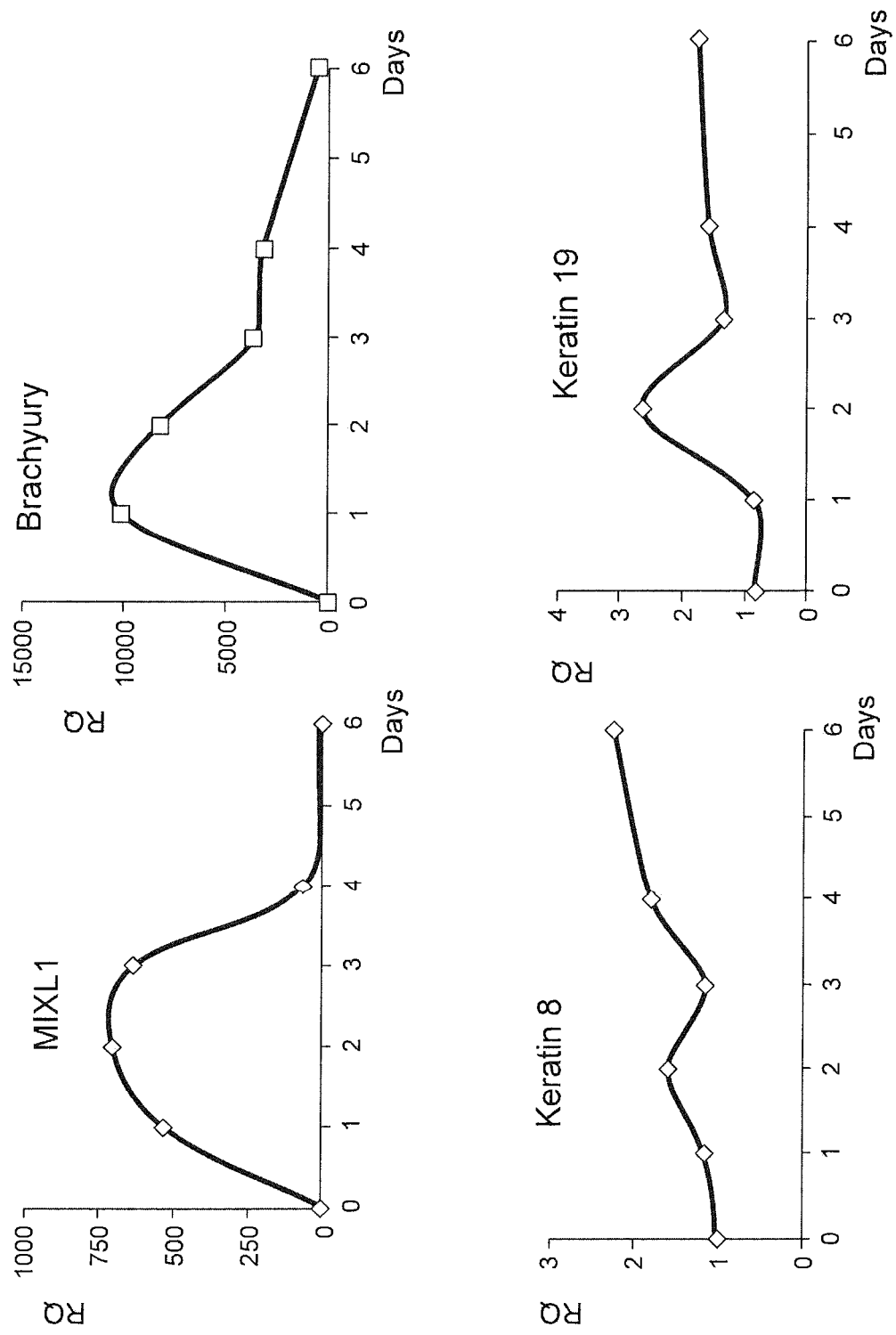

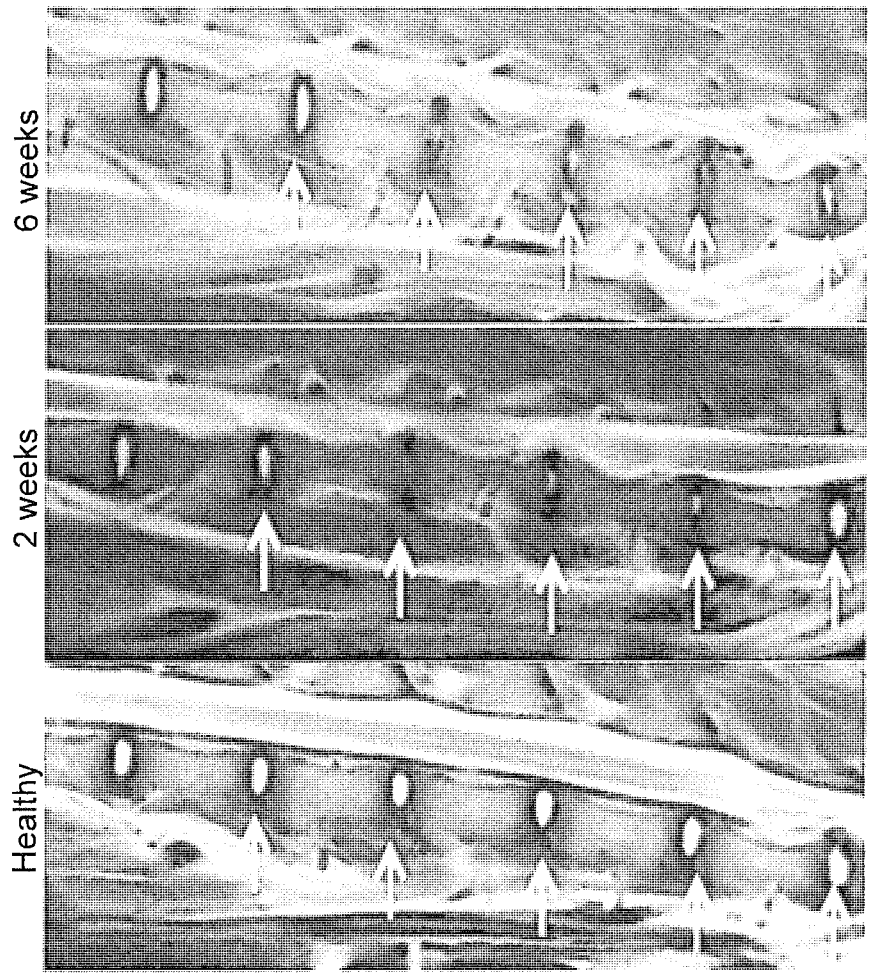
FIG. 17B
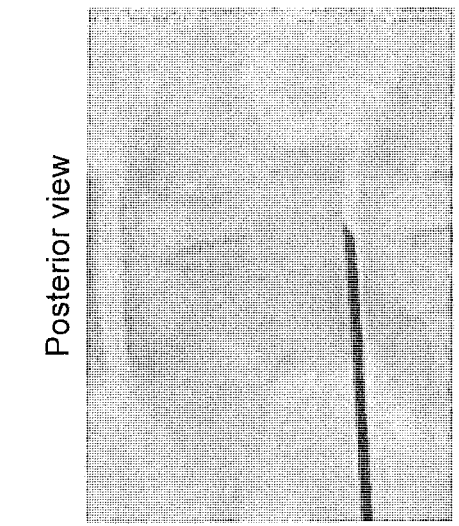
FIG. 17A

SEQUENCE LISTING

```
<160> NUMBER OF SEQ ID NOS: 3

<210> SEQ ID NO 1
<211> LENGTH: 2500
<212> TYPE: DNA
<213> ORGANISM: Homo sapiens

<400> SEQUENCE: 1
ggaggacact tctcagaagg ggttgttttg cttttgctta tttccgtcca tttccctctc      60
tgcgcgcgga ccttcctttt ccagatggtg agagccgcgg ggacacccga cgccggggca    120
ggctgatcca cgatcctggg tgtgcgtaac gccgcctggg gctccgtggg cgagggacgt    180
gtggggacag gtgcaccgga aactgccaga ctggagagtt gaggcatcgg aggcgcgaga    240
```

```
acagcactac tactgcggcg agacgagcgc ggcgcatccc aaagcccggc caaatgcgct      300
cgtccctggg aggggaggga ggcgcgcctg gagcggggac agtcttggtc cgcgccctcc      360
tcccgggtct gtgccgggac ccgggacccg ggagccgtcg caggtctcgg tccaaggggc      420 ccctttctc ggaagggcgg cggccaagag cagggaaggt ggatctcagg tagcgagtct       480
gggcttcggg gacggcgggg aggggagccg gacgggagga tgagctcccc tggcaccgag      540
agcgcgggaa agagcctgca gtaccgagtg gaccacctgc tgagcgccgt ggagaatgag      600
ctgcaggcgg gcagcgagaa gggcgacccc acagagcgcg aactgcgcgt gggcctggag      660
gagagcgagc tgtggctgcg cttcaaggag ctcaccaatg agatgatcgt gaccaagaac      720
ggcaggagga tgtttccggt gctgaaggtg aacgtgtctg gcctggaccc caacgccatg      780
tactccttcc tgctggactt cgtggcggcg gacaaccacc gctggaagta cgtgaacggg      840
gaatgggtgc cggggggcaa gccggagccg caggcgccca gctgcgtcta catccacccc      900
gactcgccca acttcggggc ccactggatg aaggctcccg tctccttcag caaagtcaag      960
ctcaccaaca agctcaacgg agggggccag atcatgctga actccttgca taagtatgag     1020
cctcgaatcc acatagtgag agttgggggt ccacagcgca tgatcaccag ccactgcttc     1080
cctgagaccc agttcatagc ggtgactgct tatcagaacg aggagatcac agctcttaaa     1140
attaagtaca atccatttgc aaaagctttc cttgatgcaa aggaaagaag tgatcacaaa     1200
gagatgatga ggaacccggg agacagccag caacctgggt actcccaatg ggggtggctt     1260
cttcctggaa ccagcaccct gtgtccacct gcaaatcctc atcctcagtt tggaggtgcc     1320 ctctcccctcc cctccacgca cagctgtgac aggtacccaa ccctgaggag ccaccggtcc     1380
tcaccctacc ccagccccta tgctcatcgg aacaattctc caacctattc tgacaactca     1440
cctgcatgtt tatccatgct gcaatcccat gacaattggt ccagccttgg aatgcctgcc     1500
catcccagca tgctccccgt gagccacaat gccagcccac ctaccagctc cagtcagtac     1560
cccagcctgt ggtctgtgag caacggcgcc gtcaccccgg gctcccaggc agcagccgtg     1620
tccaacgggc tgggggccca gttcttccgg ggctccccg cgcactacac acccctcacc      1680
catccggtct cggcgccctc ttcctcggga tccccactgt acgaaggggc ggccgcggcc     1740
acagacatcg tggacagcca gtacgacgcc gcagcccaag gccgcctcat agcctcatgg     1800
acacctgtgt cgccacccttc catgtgaagc agcaaggccc aggtcccgaa agatgcagtg     1860 acttttgtc gtggcagcca gtggtgactg gattgaccta ctaggtaccc agtggcagtc      1920
tcaggttaag aaggaaatgc agcctcagta acttccttt caaagcagtg gaggagcaca      1980
cggcaccttt ccccagagcc ccagcatccc ttgctcacac ctgcagtagc ggtgctgtcc     2040
caggtggctt acagatgaac ccaactgtgg agatgatgca gttggcccaa cctcactgac     2100
ggtgaaaaaa tgtttgccag ggtccagaaa cttttttttgg tttatttctc atacagtgta    2160
ttggcaactt tggcacacca gaatttgtaa actccaccag tcctacttta gtgagataaa     2220
aagcacactc ttaatcttct tccttgttgc tttcaagtag ttagagttga gctgttaagg     2280
acagaataaa atcatagttg aggacagcag gttttagttg aattgaaaat ttgactgctc     2340 tgcccctag aatgtgtgta ttttaagcat atgtagctaa tctcttgtgt tgttaaacta      2400
taactgtttc atattttct tttgacaaag tagccaaaga caatcagcag aaagcatttt      2460
ctgcaaaata aacgcaatat gcaaaaaaaa aaaaaaaa                             2500
```

<210> SEQ ID NO 2
<211> LENGTH: 2233

```
<212> TYPE: DNA
<213> ORGANISM: Homo sapiens

<400> SEQUENCE: 2
ggaggacact tctcagaagg ggttgttttg cttttgctta tttccgtcca tttccctctc      60
tgcgcgcgga ccttccttt  ccagatggtg agagccgcgg ggacacccga cgccggggca     120
ggctgatcca cgatcctggg tgtgcgtaac gccgcctggg gctccgtggg cgagggacgt     180
gtggggacag gtgcaccgga aactgccaga ctggagagtt gaggcatcgg aggcgcgaga     240
acagcactac tactgcggcg agacgagcgc ggcgcatccc aaagcccggc caaatgcgct     300
cgtccctggg aggggaggga ggcgcgcctg agcggggac  agggcggcgg ccaagagcag     360
ggaaggtgga tctcaggtag cgagtctggg cttcggggac ggcggggagg ggagccggac     420
gggaggatga gctcccctgg caccgagagc gcgggaaaga gcctgcagta ccgagtggac     480
cacctgctga gcgccgtgga gaatgagctg caggcgggca gcgagaaggg cgaccccaca     540
gagcgcgaac tgcgcgtggg cctggaggag agcgagctgt ggctgcgctt caaggagctc     600
accaatgaga tgatcgtgac caagaacggc aggaggatgt ttccggtgct gaaggtgaac     660
gtgtctggcc tggaccccaa cgccatgtac tccttcctgc tggacttcgt ggcggcggac     720
aaccaccgct ggaagtacgt gaacggggaa tgggtgccgg ggggcaagcc ggagccgcag     780
gcgcccagct gcgtctacat ccaccccgac tcgcccaact tcggggccca ctggatgaag     840
gctcccgtct ccttcagcaa agtcaagctc accaacaagc tcaacggagg gggccagatc     900
atgctgaact ccttgcataa gtatgagcct cgaatccaca tagtgagagt tgggggtcca     960
cagcgcatga tcaccagcca ctgcttccct gagacccagt tcatagcggt gactgcttat    1020
cagaacgagg agatcacagc tcttaaaatt aagtacaatc catttgcaaa agctttcctt    1080
gatgcaaagg aaagaagtga tcacaaagag atgatggagg aacccggaga cagccagcaa    1140
cctgggtact cccaatccta ttctgacaac tcacctgcat gtttatccat gctgcaatcc    1200
catgacaatt ggtccagcct tggaatgcct gcccatccca gcatgctccc cgtgagccac    1260
aatgccagcc cacctaccag ctccagtcag taccccagcc tgtggtctgt gagcaacggc    1320
gccgtcaccc cgggctccca ggcagcagcc gtgtccaacg gctgggggc  ccagttcttc    1380
cggggctccc ccgcgcacta cacacccctc acccatccgg tctcggcgcc ctcttcctcg    1440
ggatccccac tgtacgaagg ggcggccgcg gccacagaca tcgtggacag ccagtacgac    1500
gccgcagccc aaggccgcct catagcctca tggacacctg tgtcgccacc ttccatgtga    1560
agcagcaagg cccaggtccc gaaagatgca gtgactttt  gtcgtggcag ccagtggtga    1620
ctggattgac ctactaggta cccagtggca gtctcaggtt aagaaggaaa tgcagcctca    1680
gtaacttcct tttcaaagca gtggaggagc acacggcacc tttccccaga gccccagcat    1740
cccttgctca cacctgcagt agcggtgctg tcccaggtgg cttacagatg aacccaactg    1800
tggagatgat gcagttggcc caacctcact gacggtgaaa aatgtttgc  cagggtccag    1860
aaactttttt tggtttattt ctcatacagt gtattggcaa ctttggcaca ccagaatttg    1920
taaactccac cagtcctact ttagtgagat aaaaagcaca ctcttaatct tcttccttgt    1980
tgctttcaag tagttagagt tgagctgtta aggacagaat aaaatcatag ttgaggacag    2040
caggttttag ttgaattgaa aatttgactg ctctgccccc tagaatgtgt gtattttaag    2100
catatgtagc taatctcttg tgttgttaaa ctataactgt ttcatatttt tcttttgaca    2160
aagtagccaa agacaatcag cagaaagcat tttctgcaaa ataaacgcaa tatgcaaaaa    2220
```
aaaaaaaaaa aaa                                                         2233

<210> SEQ ID NO 3
<211> LENGTH: 6598
<212> TYPE: DNA
<213> ORGANISM: Artificial Sequence
<220> FEATURE:
<223> OTHER INFORMATION: pCMV6-AC-GFP

<400> SEQUENCE: 3

| | | | | |
|---|---|---|---|---|
| aacaaaatat | taacgcttac | aatttccatt | cgccattcag gctgcgcaac tgttgggaag | 60 |
| ggcgatcggt | gcgggcctct | tcgctattac | gccagctggc gaaaggggga tgtgctgcaa | 120 |
| ggcgattaag | ttgggtaacg | ccagggtttt | cccagtcacg acgttgtaaa acgacggcca | 180 |
| gtgccaagct | gatctataca | ttgaatcaat | attggcaatt agccatatta gtcattggtt | 240 |
| atatagcata | aatcaatatt | ggctattggc | cattgcatac gttgtatcta tatcataata | 300 |
| tgtacattta | tattggctca | tgtccaatat | gaccgccatg ttgacattga ttattgacta | 360 |
| gttattaata | gtaatcaatt | acgggtcat | tagttcatag cccatatatg gagttccgcg | 420 |
| ttacataact | tacggtaaat | ggcccgcctg | gctgaccgcc caacgacccc cgcccattga | 480 |
| cgtcaataat | gacgtatgtt | cccatagtaa | cgccaatagg gactttccat tgacgtcaat | 540 |
| gggtggagta | tttacggtaa | actgcccact | ggcagtaca tcaagtgtat catatgccaa | 600 |
| gtccgccccc | tattgacgtc | aatgacggta | aatggcccgc ctggcattat gcccagtaca | 660 |
| tgaccttacg | ggactttcct | acttggcagt | acatctacgt attagtcatc gctattacca | 720 |
| tggtgatgcg | gttttggcag | tacaccaatg | ggcgtggata gcggtttgac tcacggggat | 780 |
| ttccaagtct | ccacccccatt | gacgtcaatg | ggagtttgtt ttggcaccaa aatcaacggg | 840 |
| actttccaaa | atgtcgtaat | aaccccgccc | cgttgacgca aatgggcggt aggcgtgtac | 900 |
| ggtgggaggt | ctatataagc | agagctcgtt | tagtgaaccg tcagaatttt gtaatacgac | 960 |
| tcactatagg | gcgccggga | attcgtcgac | tggatccggt accgaggaga tctgccgccg | 1020 |
| cgatcgccgg | cgcgccagat | ctcaagctta | actagttagc ggaccgacgc gtacgcggcc | 1080 |
| gctcgagatg | gagagcgacg | agagcggcct | gccgccatg gagatcgagt gccgcatcac | 1140 |
| cggcaccctg | aacggcgtgg | agttcgagct | ggtgggcggc ggagagggca cccccgagca | 1200 |
| gggccgcatg | accaacaaga | tgaagagcac | caaaggcgcc ctgaccttca gcccctacct | 1260 |
| gctgagccac | gtgatgggct | acggcttcta | ccacttcggc acctaccccc gcggctacga | 1320 |
| gaacccctc | ctgcacgcca | tcaacaacgg | cggctacacc aacacccgca tcgagaagta | 1380 |
| cgaggacggc | ggcgtgctgc | acgtgagctt | cagctaccgc tacgaggccg ccgcgtgat | 1440 |
| cggcgacttc | aaggtgatgg | gcaccggctt | ccccgaggac agcgtgatct tcaccgacaa | 1500 |
| gatcatccgc | agcaacgcca | ccgtggagca | cctgcacccc atgggcgata acgatctgga | 1560 |
| tggcagcttc | acccgcacct | tcagcctgcg | cgacggcggc tactacagct ccgtggtgga | 1620 |
| cagccacatg | cacttcaaga | gcgccatcca | ccccagcatc ctgcagaacg ggggccccat | 1680 |
| gttcgccttc | cgccgcgtgg | aggaggatca | cagcaacacc gagctgggca tcgtggagta | 1740 |
| ccagcacgcc | ttcaagaccc | cggatgcaga | tgccggtgaa gaaagagttt aaacggccgg | 1800 |
| ccgcggtcat | agctgtttcc | tgaacagatc | ccgggtggca tccctgtgac ccctccccag | 1860 |
| tgcctctcct | ggccctggaa | gttgccactc | cagtgcccac cagccttgtc ctaataaaat | 1920 |
| taagttgcat | cattttgtct | gactaggtgt | ccttctataa tattatgggg tgaggggggg | 1980 |
| tggtatggag | caaggggcaa | gttgggaaga | caacctgtag ggcctgcggg gtctattggg | 2040 |

```
aaccaagctg gagtgcagtg gcacaatctt ggctcactgc aatctccgcc tcctgggttc   2100
aagcgattct cctgcctcag cctcccgagt tgttgggatt ccaggcatgc atgaccaggc   2160
tcagctaatt tttgtttttt tggtagagac ggggtttcac catattggcc aggctggtct   2220
ccaactccta atctcaggtg atctacccac cttggcctcc caaattgctg ggattacagg   2280
cgtgaaccac tgctcccttc cctgtccttc tgattttaaa ataactatac cagcaggagg   2340
acgtccagac acagcatagg ctacctggcc atgcccaacc ggtgggacat ttgagttgct   2400 tgccttggcac tgtcctctca tgcgttgggt ccactcagta gatgcctgtt gaattgggta   2460
cgcggccagc ttggctgtgg aatgtgtgtc agttagggtg tggaaagtcc ccaggctccc   2520
cagcaggcag aagtatgcaa agcatgcatc tcaattagtc agcaaccagg tgtggaaagt   2580
ccccaggctc cccagcaggc agaagtatgc aaagcatgca tctcaattag tcagcaacca   2640
tagtcccgcc cctaactccg cccatcccgc ccctaactcc gcccagttcc gcccattctc   2700
cgccccatgg ctgactaatt ttttttattt atgcagagc cgaggccgcc tcggcctctg   2760
agctattcca gaagtagtga ggaggctttt ttggaggcct aggcttttgc aaaaagctcc   2820
cgggagcttg tatatccatt ttcggatctg atcaagagac aggatgagga tcgtttcgca   2880
tgattgaaca agatggattg cacgcaggtt ctccggccgc ttgggtggag aggctattcg   2940
gctatgactg ggcacaacag acaatcggct gctctgatgc cgccgtgttc cggctgtcag   3000
cgcaggggcg cccggttctt tttgtcaaga ccgacctgtc cggtgccctg aatgaactgc   3060
aggacgaggc agcgcggcta tcgtggctgg ccacgacggg cgttccttgc gcagctgtgc   3120
tcgacgttgt cactgaagcg ggaagggact ggctgctatt gggcgaagtg ccggggcagg   3180
atctcctgtc atctcacctt gctcctgccg agaaagtatc catcatggct gatgcaatgc   3240
ggcggctgca tacgcttgat ccggctacct gcccattcga ccaccaagcg aaacatcgca   3300
tcgagcgagc acgtactcgg atggaagccg gtcttgtcga tcaggatgat ctggacgaag   3360
agcatcaggg gctcgcgcca gccgaactgt tcgccaggct caaggcgcgc atgcccgacg   3420
gcgaggatct cgtcgtgacc catggcgatg cctgcttgcc gaatatcatg gtggaaaatg   3480
gccgcttttc tggattcatc gactgtgcc ggctgggtgt ggccgaccgc tatcaggaca   3540
tagcgttggc tacccgtgat attgctgaag agcttggcgg cgaatgggct gaccgcttcc   3600
tcgtgcttta cggtatcgcc gctcccgatt cgcagcgcat cgccttctat cgccttcttg   3660
acgagttctt ctgagcggga ctctggggtt cgaaatgacc gaccaagcga cgcccaacct   3720
gccatcacga gatttcgatt ccaccgccgc cttctatgaa aggttgggct tcggaatcgt   3780
tttccgggac gccggctgga tgatcctcca gcgcgggat tcatgctgg agttcttcgc   3840 ccaccccaac ttgtttattg cagcttataa tggttacaaa taaagcaata gcatcacaaa   3900
tttcacaaat aaagcatttt tttcactgca ttctagttgt ggtttgtcca aactcatcaa   3960
tgtatcttat catgtctgta taccgtcgac ctctagctag agcttggcgt aatcatggtc   4020
atagctgttt cctgtgtgaa attgttatcc gctcacaatt ccacacaaca tacgagccgg   4080
aagcataaag tgtaaagcct ggggtgccta atgagtgagc taactcacat taattgcgtt   4140
gcgctcactg cccgctttcc agtcgggaaa cctgtcgtgc cagctgcatt aatgaatcgg   4200
ccaacgcgcg gggagaggcg gtttgcgtat tgggcgctct tccgcttcct cgctcactga   4260
ctcgctgcgc tcggtcgttc ggctgcgcg agcggtatca gctcactcaa aggcggtaat   4320
acggttatcc acagaatcag gggataacgc aggaaagaac atgtgagcaa aaggccagca   4380
```

-continued

| | |
|---|---|
| aaaggccagg aaccgtaaaa aggccgcgtt gctggcgttt tccataggcc tccgcccccc | 4440 |
| tgacgagcat cacaaaaatc gacgctcaag tcagaggtgg cgaaacccga caggactata | 4500 |
| aagataccag gcgtttcccc ctggaagctc cctcgtgcgc tctcctgttc cgaccctgcc | 4560 |
| gcttaccgga tacctgtccg cctttctccc ttcgggaagc gtggcgcttt ctcatagctc | 4620 |
| acgctgtagg tatctcagtt cggtgtaggt cgttcgctcc aagctgggct gtgtgcacga | 4680 |
| accccccgtt cagcccgacc gctgcgcctt atccggtaac tatcgtcttg agtccaaccc | 4740 |
| ggtaagacac gacttatcgc cactggcagc agccactggt aacaggatta gcagagcgag | 4800 |
| gtatgtaggc ggtgctacag agttcttgaa gtggtggcct aactacggct acactagaag | 4860 |
| aacagtattt ggtatctgcg ctctgctgaa gccagttacc ttcggaaaaa gagttggtag | 4920 |
| ctcttgatcc ggcaaacaaa ccaccgctgg tagcggtttt tttgtttgca agcagcagat | 4980 |
| tacgcgcaga aaaaaggat ctcaagaaga tcctttgatc ttttctacgg ggtctgacgc | 5040 |
| tcagtggaac gaaaactcac gttaagggat tttggtcatg agattatcaa aaaggatctt | 5100 |
| cacctagatc cttttaaatt aaaaatgaag ttttaaatca atctaaagta tatatgagta | 5160 |
| aacttggtct gacagttacc aatgcttaat cagtgaggca cctatctcag cgatctgtct | 5220 |
| atttcgttca tccatagttg cctgactccc cgtcgtgtag ataactacga tacgggaggg | 5280 |
| cttaccatct ggccccagtg ctgcaatgat accgcgagac ccacgctcac cggctccaga | 5340 |
| tttatcagca ataaccagc cagccggaag ggccgagcgc agaagtggtc ctgcaacttt | 5400 |
| atccgcctcc atccagtcta ttaattgttg ccgggaagct agagtaagta gttcgccagt | 5460 |
| taatagtttg cgcaacgttg ttgccattgc tacaggcatc gtggtgtcac gctcgtcgtt | 5520 |
| tggtatggct tcattcagct ccggttccca acgatcaagg cgagttacat gatccccat | 5580 |
| gttgtgcaaa aaagcggtta gctccttcgg tcctccgatc gttgtcagaa gtaagttggc | 5640 |
| cgcagtgtta tcactcatgg ttatggcagc actgcataat tctcttactg tcatgccatc | 5700 |
| cgtaagatgc ttttctgtga ctggtgagta ctcaaccaag tcattctgag aatagtgtat | 5760 |
| gcggcgaccg agttgctctt gcccggcgtc aatacgggat aataccgcgc cacatagcag | 5820 |
| aactttaaaa gtgctcatca ttggaaaacg ttcttcgggg cgaaaactct caaggatctt | 5880 |
| accgctgttg agatccagtt cgatgtaacc cactcgtgca cccaactgat cttcagcatc | 5940 |
| ttttactttc accagcgttt ctgggtgagc aaaaacagga aggcaaaatg ccgcaaaaaa | 6000 |
| gggaataagg gcgacacgga aatgttgaat actcatactc ttcctttttc aatattattg | 6060 |
| aagcatttat cagggttatt gtctcatgag cggatacata tttgaatgta tttagaaaaa | 6120 |
| taaacaaata ggggttccgc gcacatttcc ccgaaaagtg ccacctgacg cgccctgtag | 6180 |
| cggcgcatta agcgcggcgg gtgtggtggt tacgcgcagc gtgaccgcta cacttgccag | 6240 |
| cgccctagcg cccgctcctt tcgctttctt cccttccttt ctcgccacgt tcgccggctt | 6300 |
| tccccgtcaa gctctaaatc gggggctccc tttagggttc cgatttagtg ctttacggca | 6360 |
| cctcgacccc aaaaaacttg attagggtga tggttcacgt agtgggccat cgccctgata | 6420 |
| gacggttttt cgccctttga cgttggagtc acgttctttt aatagtggac tcttgttcca | 6480 |
| aactggaaca acactcaacc ctatctcggt ctattctttt gatttataag ggattttgcc | 6540 |
| gatttcggcc tattggttaa aaaatgagct gatttaacaa aaatttaacg cgaattttt | 6598 |

METHOD FOR REGENERATING THE INTERVERTERBRAL DISC WITH NOTOCHORDAL CELLS

CROSS-REFERENCE TO RELATED APPLICATIONS

This application is a National Phase of International Application No. PCT/US2016/038799 filed Jun. 22, 2016, which designated the U.S. and that International Application was published under PCT Article 21(2) in English, which also includes a claim of priority under 35 U.S.C. §119(e) to U.S. provisional patent application No. 62/182,816 filed Jun. 22, 2015, the entirety of which is hereby incorporated by reference.

FIELD OF THE INVENTION

Described are methods and compositions for bone and bone-related tissue degeneration and related conditions. Notochordal cells derived from pluripotent stem cells can establish new therapies related to regeneration and repair of tissue.

BACKGROUND

Low back pain (LBP) is a crippling physical and socio-economic burden with costs in the United States alone approaching $200 billion annually. This condition affects up to 80% of adults at least once during their lifetime. Degeneration of the intervertebral disc is associated with, and has been proposed to be a cause of, a large percentage of these cases of LBP. Degeneration of the disc is a chronic, progressive disease, and current clinical strategies, including both surgical as well as non-surgical approaches aimed at symptomatic relief, have done very little to improve mental, physical, or social health of those patients affected. As a result, the research community continues to focus on understanding the molecular nature of the healthy intervertebral disc and its degeneration, with the hope that novel therapeutic and regenerative strategies will eventually be developed to more adequately treat patients with the disabling condition of excessive and pathological disc degeneration.

The intervertebral disc contains three distinct tissue compartments. The outer fibrocartilaginous annulus fibrosus (AF) and the superior and inferior cartilaginous endplates completely enclose the gel-like nucleus pulposus (NP), an avascular, aggrecan-rich tissue. It is generally understood that notochord cells (NCs) do not exist in adult humans, instead they are a transient embryonic population disappearing during early human development. The NP is frequently implicated in disc degeneration and, as such, has been the focus of much research in the basic science and tissue engineering fields. In spite of this, a consensus is lacking in defining the young healthy, NP cell phenotype, and furthermore, there may be limits for repair and regeneration processes conferred by NP cells, or NP-like cells. Interestingly, animals in which NCs remain throughout the majority of their lifespan, including commonly used experimental animals such as rabbits, rats, and mice, do not show signs of degeneration and maintain a more hydrated, proteoglycan-rich matrix than that found in adult human NP tissue. Supporting this theory, NCs were found to be more metabolically active and to produce more proteoglycans (PGs) than smaller NP cells. Yet, some have argued that NP cells, or NP-like cells are essentially the same as notochord (NC) cells, and it should be said that definitive characterization of both populations (e.g., NP and NC) is lacking. Compounding such technical challenges, human NCs are in short supply, due to their disappearance during childhood, and cannot be harvested as an autologous or allogeneic graft. An alternative source of NCs is thus needed, and a potential strategy would be to mimic the differentiation process that occurs during embryogenesis and obtain NCs from pluripotent stem cells.

Current treatments for DDD rely on conservative therapies (pain management and exercise) and surgical treatments such as spinal fusion and disc replacement, which have complications and poor long-term clinical outcomes. Despite decades of research, robust clinical therapies targeting underlying causes rather than symptoms are still in the earliest stages of development. One can attempt to define the NP cell phenotype as a collection of "markers"—genes, proteins, and metabolic characteristics that are representative and distinguishing of NP cells. Nevertheless, it is important to focus on defining a phenotype, rather than merely a genotype, since phenotypic characteristics likely have physiologic consequences and dictate NP cell function vital for identifying suitable therapeutic material. With such a functional phenotypic definition of therapeutic material, one can more easily distinguish NP cells from AF cells and other related cell types, better diagnose degenerate conditions, and gauge therapies while comparing healthy and degenerate samples, and better guide stem cell and tissue engineering strategies that attempt to replace lost NP cells and tissue. Perhaps most important, a clear identification of phenotype will allow us to better understand the physiology and function of NP cells, ultimately driving development of novel cell-based therapeutic modalities. Phenotypic characterization of NP cells at all stages of development, growth, maturation, and disease warrant further characterization and identification, including confirmation of the properties of bona fide human NCs.

Notochordal cells are attractive candidates for cell therapy for intervertebral discs (IVDs), since the cells have a critical function in disc generation and their disappearance is associated with disc degeneration. Based on the Inventors' previous work, it is established that stem cells residing in the degenerate disc are impaired in their potential to regenerate the disc. Described herein is a reproducible and inexhaustible source of iPSC-derived NCs (iNCs). By characterizing these cells to ensure that they have acquired NC functionality and the potential to rejuvenate the IVD, the results described herein show that iNCs can be generated from iPSCs in a two-step process, in which the cells are first transformed into primitive streak cells using GSK3i and then reprogrammed into NCs using overexpression of the Brachyury gene. By developing a method of IVD regeneration using human iNCs, it is established that: i) iPSCs can be directed to differentiate into NCs in a two-step process that includes Brachyury transcription factor overexpression; ii) iNCs will function appropriately to stimulate cell viability, gene expression of cell differentiation, further including matrix protein secretion in nucleus pulposus cell (NPC)/iNC co-cultures exposed to mechanical loading conditions that simulate IVD degeneration in vitro; and iii) iNCs will induce regeneration of the degenerate IVD in vivo.

SUMMARY OF THE INVENTION

Described herein is a method for modulating intervertebral disc degeneration, comprising selecting a subject, and administering a quantity of induced notochordal cells (iNCs), wherein administering the iNCs modulates intervertebral disc degeneration in the subject. In other embodiments, the iNCs express one or more markers Galectin 3, chondroitin sulfate epitopes (3B3, 7D4, 4C3), Vimentin, Noggin, Integrins (a1, b1, a5, a6), and Brachyury. In other embodiments, the iNCs express one or more markers homeobox MIXL1, Brachyury, Noggin, Keratin 8 and Keratin 19. In other embodiments, the iNCs are encapsulated in a hydrogel. In other embodiments, the hydrogel includes PuraMatrix® peptide hydrogel. In other embodiments, the hydrogel includes Fibrinogen-Tetronic-1307 1 KPa hydrogel. In other embodiments, at least about $1\times10^6$, $2\times10^6$, or $3\times10^6$ or more iNCs are administered to the subject. In other embodiments, modulating intervertebral disc degeneration includes an increase in water content and/or disc height. In other embodiments, modulating intervertebral disc degeneration includes an increase in proteoglycan-matrix in nuclear pulposus tissue.

Also described herein is a method of generating induced notochordal cells (iNCs) including providing a quantity of induced pluripotent stem cells (iPSCs), culturing the iPSCs in the presence of a GSK3 inhibitor (GSK3i) to form primitive streak (PS) cells, contacting the PS cells with a vector encoding Brachyury, and expressing Brachyury in the PS cells, wherein expressing Brachyury in the PS cells induces formation of induced notochordal cells (iNCs). In other embodiments, the iPSCs are cultured in the presence of about 1, 2, 3, 4, 5, 6, 7, 8, 9, or 10 µM of GSK3i. In other embodiments, the iPSCs are cultured in the presence of GSK3i for 1, 2, 3, 4, 5, 6, 7, or 8 days. In other embodiments, contacting the PS cells with a vector includes nucleofection. In other embodiments, contacting the PS cells with a vector includes transfection. In other embodiments, expressing Brachyury in the PS cells includes culturing the PS cells in A-RPMI media. In other embodiments, culturing the PS cells in A-RPMI media is for about 5, 6, or 7 or more days. In other embodiments, the methods includes exogenous addition of one or more of FGF, Noggin, and dickkopf 1 (DKK1) to the Brachyury expressing PS cells.

Further described herein is composition of iNCs made by the method of generating induced notochordal cells (iNCs) including providing a quantity of induced pluripotent stem cells (iPSCs), including the iPSCs in the presence of a GSK3 inhibitor (GSK3i) to form primitive streak (PS) cells, contacting the PS cells with a vector encoding Brachyury, and expressing Brachyury in the PS cells, wherein expressing Brachyury in the PS cells induces formation of induced notochordal cells (iNCs). In other embodiments, the iPSCs are cultured with about 1, 2, 3, 4, 5, 6, 7, 8, 9, or 10 µM of GSK3i. In other embodiments, the culturing in the presence of GSK3i is for 1, 2, 3, 4, 5, 6, 7, or 8 days. In other embodiments, contacting the PS cells with a vector comprises nucleofection. In other embodiments, contacting the PS cells with a vector comprises transfection. In other embodiments, expressing Brachyury in the PS cells comprises culturing the PS cells in A-RPMI media. In other embodiments, culturing the PS cells in A-RPMI media is for about 5, 6, or 7 or more days. In other embodiments, the methods includes exogenous addition of one or more of FGF, Noggin, and dickkopf 1 (DKK1) to the Brachyury expressing PS cells.

Also described herein is a composition of induced notochordal cells (iNCs). In other embodiments, the iNCs express one or more markers Galectin 3, chondroitin sulfate epitopes (3B3, 7D4, 4C3), Vimentin, Noggin, Integrins (a1, b1, a5, a6), and Brachyury. In other embodiments, the iNCs express one or more markers homeobox MIXL1, Brachyury, Noggin, Keratin 8 and Keratin 19.

BRIEF DESCRIPTION OF FIGURES

FIG. 1. Notochordal cells can be separated from nuclear pulposus (NP) cells based on size. (FIG. 1A) Porcine IVDs were harvested from healthy pigs. (FIG. 1B) Porcine NPs were enzymatially digested with 0.25% collagenase and 1% hyaluronidase overnight. The cells were washed, and notochordal cell clusters were separated from the small NP cells using a 70-µm cell strainer. (FIG. 1C) The RNA of each population was extracted, analyzed and ploted with RQ values comparing to total NP cells. Gene expression analysis of genes typically expressed in NP cells (blue) showed higher levels of expression in small cells than in larger cell clusters. Genes that were previously observed to be expressed in notochordal cells (red) were highly expressed in large cell clusters compared with that in small cells. These findings are consistent with those of previous studies and show that when separated by size, notochordal cells can be used as a positive control.

FIG. 2. Step 1—Differentiation of iPSCs into primitive streak (PS) cells in vitro. iPSCs were cultured with addition of 5µM GSK3i for up to 6 days. (FIG. 2A). Morphological changes during treatment were depicted with light microscopy. (FIG. 2B). On Days 2 and 4 mesenchymal stem cell (MSC) markers CD44 and CD90 were expressed at high levels, similar to what occurs in bone marrow-derived human MSCs (BM-hMSCs). The NC/NP marker CD24 was expressed in PS cells but not in BM-MSCs. (FIG. 2C). Gene expression analysis of the PS cells over time showed peak expression of mesodermal markers MIXL1 and Brachyury on Day 2 and a gradual increase in NC markers Keratins 8 and 19.

(FIG. 4A B) PS-Br cells were fixed 4 days after nucleofection and stained against Brachyury and Glut4 epitopes using immunofluorescence (IF). The IF indicates high expression of Brachyury (upper right) inside the cell nucleus mostly, but not only, in iNCs, and expression of the Glut4 NP marker mostly in iNPs (upper left).

(FIG. 8A) Three levels of degenerate IVDs following annular injury (yellow arrows) and healthy IVDs (white arrows) imaged by MRI. (FIG. 8B) Injection into the porcine IVD under fluoroscopic guidance. (FIG. 8C) An uncompromised IVD was washed out using warm saline solution and (FIG. 8D) green solution—labeled fibrin gel was injected into the void.

FIG. 13. Step 1—Differentiation of iPSCs into primitive streak (PS) cells in vitro.

FIG. 14. Step 2— Differentiation of PS cells into iNC progenitor cells.

(FIG. 17A) Three levels of IVDs were subjected to annular puncture under fluoroscopic guidance. (FIG. 17B) The degeneration process was observed using MRI. Degenerated discs are indicated with yellow arrows and healthy IVDs with white arrows.

FIG. 18: MR imaging of the IVD can detect and quantify matrix composition.

FIG. 19B shows magnification of the NP area. The injected iNCs iNCs were detected using IF staining against Brachyury and Keratin 18, and confocal microscopy (FIG. 19C). The right panel shows that the DiI-labeled iNCs expressed both genes.

DETAILED DESCRIPTION

Figure 3A:
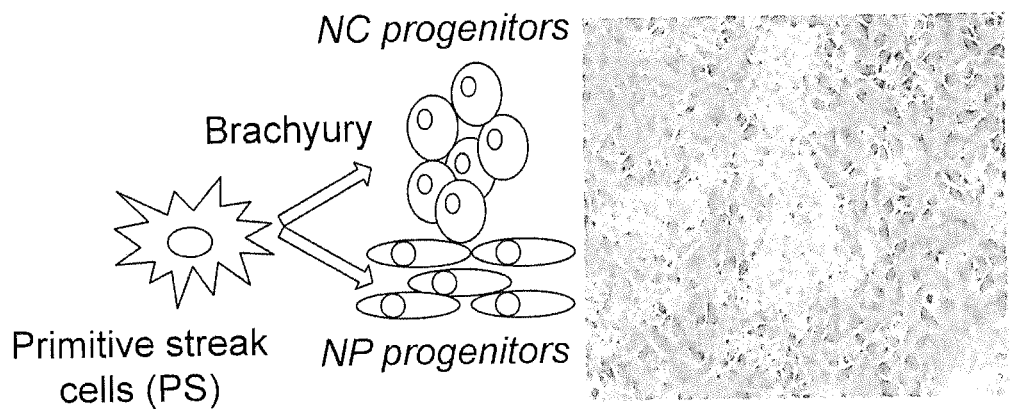
(FIG. 3A) PS cells were nucleofected with either Brachyury (Br) or GFP-encoding plasmids and cultured in A-RPMI in vitro. Light microscopy showed the formation of two layers of cells differing in morphological characteristics: fibroblast-like cells attached to the plate (iNPs) and clustered, loosely attached, round cells (iNCs) (FIG. 3B). Bars indicate SEs, *p<0.05;p<0.01; *p<0.001; ****P<0.0001, FIG. 4. Differential gene expression of iNPs and iNCs.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22nd ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology 3rd ed., revised ed.*, J. Wiley & Sons (New York, N.Y. 2006); Smith, *March's Advanced Organic Chemistry Reactions, Mechanisms and Structure 7$^{th}$ ed.*, J. Wiley & Sons (New York, N.Y. 2013); Singleton, *Dictionary of DNA and Genome Technology 3$^{rd}$ ed.*, Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual 2$^{nd}$ ed.*, Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

As described, low back pain (LBP) is a crippling physical and socioeconomic burden with costs in the United States alone approaching $200 billion annually and affecting up to 80% of adults at least once during their lifetime. Degeneration of the intervertebral disc is involved with a large percentage of these cases of LBP with current clinical strategies of surgical as well as non-surgical approaches aimed at symptomatic relief. Despite these advances there is a need for novel treatment approaches.

Imaging studies have indicated a link between LBP and intervertebral disc (IVD) degeneration in 40% of patients. IVD cells occupy only 1% of IVD volume, but they are responsible for extracellular matrix synthesis and degradation. In degeneration there is an alteration in nucleus pulposus (NP) cell biology that leads to diminished cell numbers and altered cell function, resulting in an imbalance between matrix synthesis and degradation. Proteoglycan synthesis decreases, and there is a transition from type II collagen to type I collagen. This results in a more fibrous, dehydrated matrix less able to withstand the mechanical forces experienced in the spine. These changes have been linked to the initiation of pain responses, either through direct ingrowth of nerves and blood vessels into the IVD17 or by surrounding anatomical structures (e.g., spinal facets, spinal cord), which further impair IVD function leading to pain.

Current treatments for degenerative disc disease (DDD) rely on conservative therapies such as pain management and exercise, and, when these fail, surgery. Surgical treatments such as spinal fusion and disc replacement provide satisfactory results in alleviating pain, but are not devoid of complications and poor long-term clinical outcomes. Despite decades of research, robust clinical therapies targeting underlying causes rather than symptoms are still in the earliest stages of development. Thus, there is an urgent need for alternative treatments, such as stem cell therapies, focused on correcting the underlying pathogenesis and aberrant cell biology of DDD. An appropriate cell source still needs to be identified.

TABLE 1

Therapeutic Approaches

| IVD therapy | Strength | Weaknesses |
| --- | --- | --- |
| Small molecules, anti-inflammatory factors, proteins | Relatively safe - used in clinical trials Efficient to reduce acute inflammation | Short half-life of proteins in solution Limited effect of a single factor on a complex process such as DDD |
| Gene therapy: retroviruses | Prolonged effect | Limited safety (high doses, misplaced injections, lack of control over vector expression) |
| Cell therapies: NPC, MSC, iPSC | NPC: can differentiate towards chondrocytes, reduce inflammation MSC: can be autologous, reduce inflammation, pain when injected into IVD iPSC: have the potential to become notochordal cells, safe if fully differentiated | NPC: low availability, low proliferative ability MSC: the mechanism of immunomodulation is not clear yet. In human clinical trials no regeneration of the disc was found. Cell manipulation is required for expansion. Low availability of autologous cells in elderly patients iPSC: if not differentiated can induce teratomas |

Of great interest is understanding the role of notochordal cells in the IVD. Nuclear pulposus (NP) is formed from the embryonic notochord as it segments during fetal development; the surrounding annulus fibrosus (AF) is formed from the sclerotome/mesoderm. At birth, the NP is populated by morphologically distinct, large vacuolated notochordal cells (NCs). It is important to emphasize that in some vertebrates these NCs persist throughout most of adult life, whereas in other species, including humans, these NCs gradually disappear during maturation. Such transient embryonic NCs eventually becoming undetectable and replaced by a population of smaller round cells—NP cells— believed to differentiate from NCs.

The change in cell population correlates with the initiation of degenerative changes within the disc, suggesting that the loss of NCs may be responsible. Interestingly, animals in which NCs remain throughout the majority of their lifespan, including commonly used experimental animals such as rabbits, rats, and mice, do not show signs of degeneration and maintain a more hydrated, proteoglycan-rich matrix than that found in adult human NP tissue. Supporting this theory, NCs were found to be more metabolically active and to produce more proteoglycans (PGs) than smaller NP cells. Additionally, in vitro experiments with human and bovine NP cells encapsulated in 3D hydrogels suggest that NC cells could also act as stimulators, controlling the synthesis of proteoglycans by the NP cells. These findings imply that the development of stem cell-based therapies focusing on differentiation toward a notochordal cell phenotype capable of synthesizing a proteoglycan-rich matrix and playing a protective role in a catabolic environment may be more desirable than therapies focusing on differentiation into NP cells.

The presence and effect of mechanical loading on degenerative processes in the IVD is significant considering that the main function of the IVD is to transfer mechanical axial forces. Therefore, physiological loading of the IVD is a natural stimulus and known to be essential for maintenance of cell viability and matrix biology. In contrast, mechanical overload is widely assumed to promote degeneration. For example, dynamic overloading of caprine lumbar IVD explants for 21 days at 1 Hz, altering in magnitude every 30 min (0.1 MPa and 0.4-0.8 MPa for 16 hours/day), has been shown to have catabolic effects and to result in reduced cell viability in the nucleus pulposus. Moderate cyclic compression of an IVD and stem cells co-cultured in a biomimetic matrix at 10% compression, 1 Hz for 1 hour per day, resulted in upregulation of cartilage-related markers. Therefore in vitro mechanical overloading can simulate disc degeneration as well as environmental conditions affecting a healthy disc.

For use of iPSCs as a cell source for IVD cell therapy, studies have shown the therapeutic effect of mesenchymal stem cell (MSC) injection into the IVD. And while MSCs have been found either to obtain the phenotype of NP cells, they potentially only provide a short-term solution, or actually induce mineralization and bone tissue formation in the injured IVD, which impairs the function of the IVD. Therefore, given the evidence above, NCs appear to be the ideal cell to regenerate the NP.

Unfortunately, human NCs are in short supply, due to their disappearance during childhood, and cannot be harvested as an autologous or allogeneic graft. An alternative source of NCs is thus needed, and a potential strategy would be to mimic the differentiation process that occurs during embryogenesis and obtain NCs from pluripotent stem cells. Induced pluripotent stem cells (iPSCs), first discovered in 2006, can be generated from almost any kind of somatic cell by using an integration-free method. The unlimited proliferation capacity of iPSCs, combined with their pluripotent differentiation potential, places them among the most promising stem cells for IVD therapy. Indeed, the feasibility of iPSC differentiation toward NC-like cells (hereafter referred as iNCs) was recently shown using a non-defined NP tissue matrix.

Figure 10:
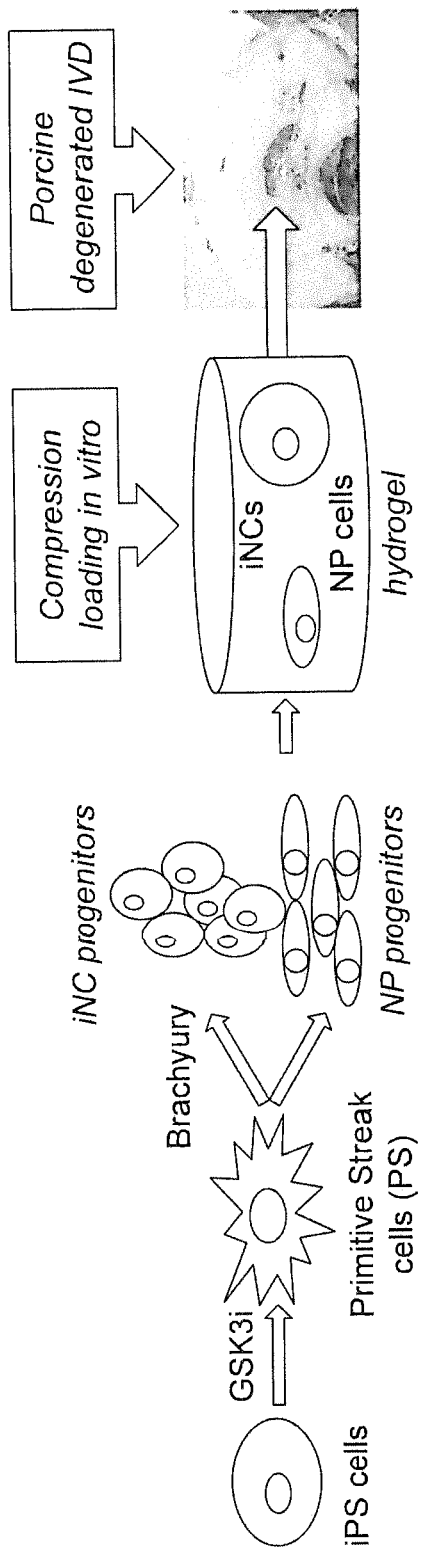
FIG. 10. Process for differentiating iPSCs into functional notochordal cells that can be used for IVD cell therapy. iPSCs can be directed to differentiate into NCs in a two-step process that includes Brachyury transcription factor overexpression. Thereafter, iNCs will function appropriately to stimulate cell viability, gene expression of cell differentiation, and matrix protein secretion in NPC/iNC co-cultures exposed to mechanical loading conditions that simulate IVD degeneration in vitro. Finally, iNCs will induce repair/regeneration of the degenerate IVD in vivo FIG. 11. Experimental design and various aims.
Figure 11:
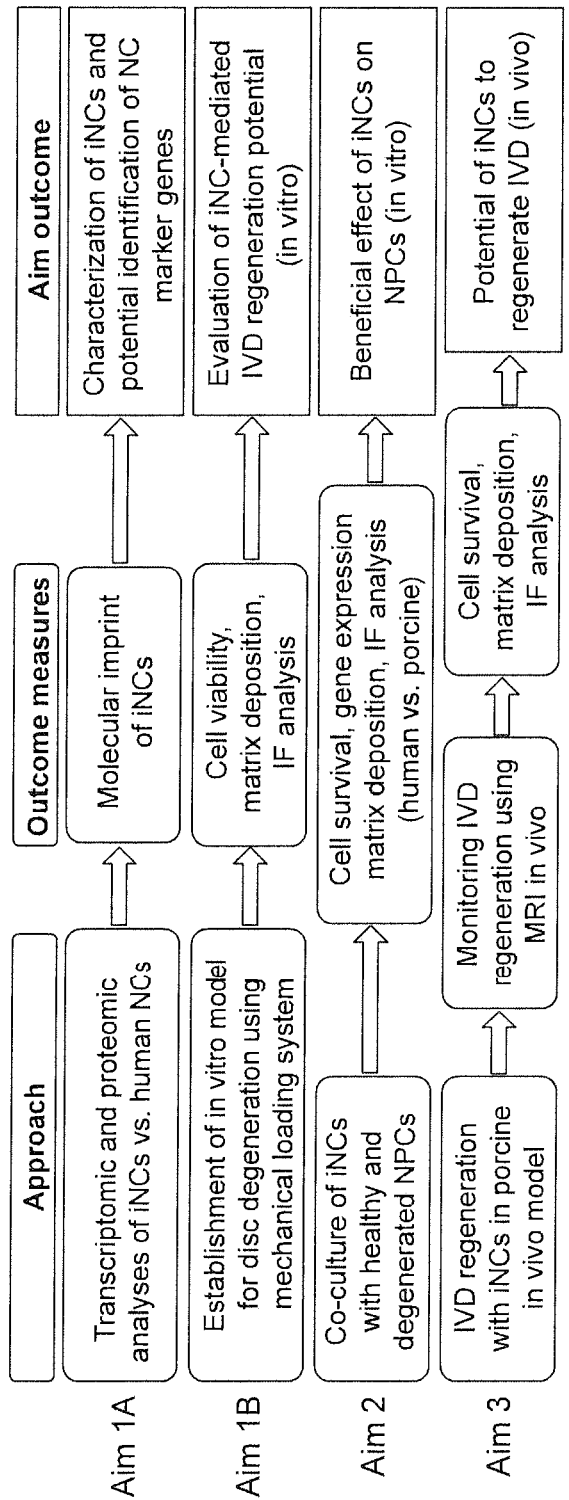
Figure 12:
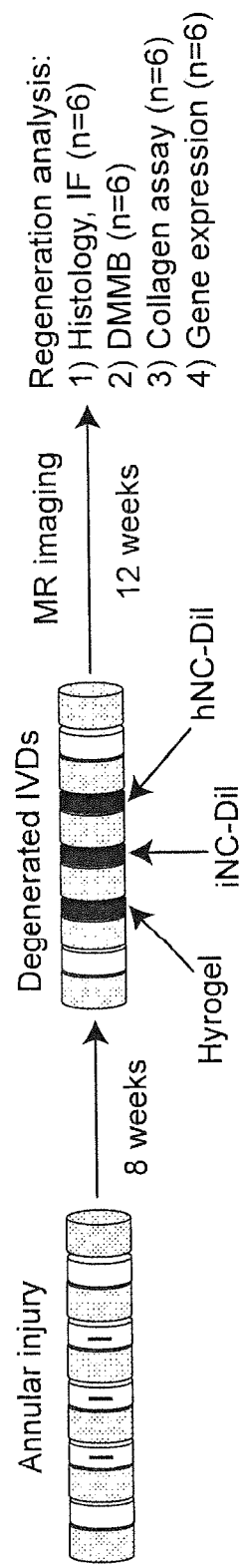
FIG. 12. Experimental design for evaluating of the regenerative potential of iNCs in a large animal model of IVD.

Described herein is a two-step, well-defined, and highly controlled method of reprogramming iPSCs into iNCs. The described approach of providing iPSC-derived NCs to the degenerate disc may reverse the course of IVD degeneration and thus rejuvenate the disc in a more permanent manner. By developing a method of regenerating degenerate IVDs by using human iPSC-derived notochordal cells it is shown that: i) iPSCs can be directed to differentiate into NCs in a two-step process that includes Brachyury transcription factor overexpression; ii) iNCs will function appropriately to stimulate cell viability, gene expression of cell differentiation, and matrix protein secretion in NPC/iNC co-cultures exposed to mechanical loading conditions that simulate IVD degeneration in vitro; and iii) iNCs will induce repair/regeneration of the degenerate IVD in vivo (FIG. 10). As iPSCs are shown as capable for differentiation into functional notochordal cells that can be used for IVD cell therapy, a reliable step-by-step method to generate iNCs that resembles human NCs in their phenotype and functional characteristics, will provide new therapeutic avenues for regeneration and repair. This includes demonstrated potential for survival and regenerative potential in in vitro and in vivo models of IVD degeneration (FIG. 11).

The Inventors are the first to tie these pieces together: deriving and comprehensively describing the NC phenotype as it has never been done before, even with NP cells, and then testing NCs' therapeutic value in simulated disc degeneration models. The Inventors' study will potentially enable the utilization of these potent cells to rejuvenate one of the most commonly degenerating tissues of the body, the nucleus pulposus. If successful, the proposed therapy could reverse the degeneration process and thereby significantly reduce the more than 650,000 spinal surgeries performed each year as well as alleviate the $50-$200 billion in annual hospital costs 14 and questionable outcomes these surgeries represent. To date, the feasibility of transforming iPSCs toward the notochordal cell-like phenotype has been reported, but in such studies iPSCs were cultured with non-defined porcine NP tissue matrix as the differentiation method. By contrast, described herein is a two-step approach that will enable a controllable differentiation process using a well-defined gene and small molecule that if developed will be more acceptable for cGMP production and FDA approval, thus having more potential to reach clinical application.

A critical feature of the described approach is molecular and functional characterization of human iPSC-derived notochordal cells (iNCs). Specifically, given the evanescent nature of NCs in humans, the goal is to compare iNCs to human NCs (obtained from young cadaveric spines) in a nucleus pulposus (NP)-mimicking environment in vitro. Therefore, characterization of the iNC molecular imprint and comparison with human NCs confirm their status as bona fide NCs. As described, while some have asserted NP cells to be equivalent to NC cells, the apparently limited capability of NP cells to regenerate and repair IVD suggests that isolation of bona fide NCs as yet unachieved. Moreover a variety of purported NC candidate cells may actually turn out to be NP-like cells, not bona fide NC cells. Confirmation of the status of bona fide NC cells would be aided greater by a extensive comparison of iNC and NC cells from young juvenile tissue, and subsequent confirmation for regeneration and repair capability in a large animal model. The iNCs will be derived from human iPSCs. Both transcriptomic and proteomic analyses will be performed on iNCs and human NCs to fully define the similarities and differences between these two phenotypes.

It is of further importance to elucidate the influence of NP-simulating mechanical loading conditions on iNCs and the cell response. Along with maturation human NCs naturally disappear from the disc before degeneration occurs; thus their therapeutic potential to treat disc degeneration is intriguing and should be investigated. Mechanical loading has been shown to be critically involved in IVD degeneration, and therefore the regenerative potential of iNCs will first be tested in vitro under defined mechanical loading conditions. Human NCs or iNCs will be encapsulated in a 3D synthetic hydrogel and stimulated by high dynamic compression to mimic the degenerated disc or by low dynamic compression, which is known to occur in healthy discs. Cell responses will be tested for viability, gene expression, and NP matrix protein secretion.

Confirming the beneficial effect of iNCs on NP cells, derived from healthy and degenerate IVDs, will rely on establishing conditions that mimic IVD degeneration in vitro. The iNCs will be compared to native human NCs in their ability to stimulate NPCs isolated from healthy or degenerated discs. NC/NPC co-cultures will be tested in 3D synthetic hydrogels under mechanical loading. Similarly treated NPCs will be used as controls. The level of NPC stimulation is evaluated by measuring the synthesis of a proteoglycan-rich matrix.

Finally, by evaluating of the regenerative potential of iNCs in a large animal model of IVD degeneration, one can assess the engraftment, survival, and differentiation potential of human iNCs in a porcine model of disc degeneration in vivo. IVD degeneration is induced using a previously published annular injury method on three spine levels (L2-5). Cells are suspended in synthetic hydrogel and injected into the nucleus pulposus. The regeneration process is monitored using MRI. Cell engraftment and differentiation is assessed after harvesting by performing an immunohistochemical analysis.

Described herein is a method for modulating intervertebral disc degeneration, comprising selecting a subject, and administering a quantity of induced notochordal cells (iNCs), wherein administering the iNCs modulates intervertebral disc degeneration in the subject. In other embodiments, the iNCs express one or more markers Galectin 3, chondroitin sulfate epitopes (3B3, 7D4, 4C3), Vimentin, Noggin, Integrins (a1, b1, a5, a6), and Brachyury. In other embodiments, the iNCs express one or more markers homeobox MIXL1, Brachyury, Noggin, Keratin 8 and Keratin 19. In other embodiments, the iNCs are encapsulated in a hydrogel. In other embodiments, the hydrogel includes PuraMatrix® peptide hydrogel. In other embodiments, the hydrogel includes Fibrinogen-Tetronic-1307 1 KPa hydrogel. In other embodiments, at least about $1\times10^6$, $2\times10^6$, $3\times10^6$, $4\times10^6$, $5\times10^6$, $6\times10^6$ or more iNCs are administered to the subject. In other embodiments, modulating intervertebral disc degeneration includes an increase in water content and/or disc height. In other embodiments, modulating intervertebral disc degeneration includes an increase in proteoglycan-matrix in nuclear pulposus (NP) tissue. In various embodiments, the iNCs are greater than about μm in size.

Also described herein is a method of generating induced notochordal cells (iNCs) including providing a quantity of induced pluripotent stem cells (iPSCs), culturing the iPSCs in the presence of a GSK3 inhibitor (GSK3i) to form primitive streak (PS) cells, contacting the PS cells with a vector encoding Brachyury, and expressing Brachyury in the PS cells, wherein expressing Brachyury in the PS cells induces formation of induced notochordal cells (iNCs). In other embodiments, the iPSCs are cultured in the presence of about 1, 2, 3, 4, 5, 6, 7, 8, 9, or 10 μM of GSK3i. In other embodiments, the iPSCs are cultured in the presence of about 4, 5, or 6 μM of GSK3i In other embodiments, the iPSCs are cultured in the presence of GSK3i for 1, 2, 3, 4, 5, 6, 7, or 8 days. In other embodiments, the iPSCs are cultured in the presence of GSK3i for 3, 4, or 5 days. In other embodiments, the iPSCs are cultured in the presence of GSK3i for about 3 days In other embodiments, the vector is pCMV6-AC-GFP vector. In other embodiments, contacting the PS cells with a vector includes nucleofection. In other embodiments, contacting the PS cells with a vector includes transfection. In other embodiments, expressing Brachyury in the PS cells includes culturing the PS cells in A-RPMI media. In other embodiments, culturing the PS cells in A-RPMI media is for about 5, 6, or 7 or more days. In other embodiments, the methods includes exogenous addition of one or more of FGF, Noggin, and dickkopf 1 (DKK1) to the Brachyury expressing PS cells.

Further described herein is composition of iNCs made by the method of generating induced notochordal cells (iNCs) including providing a quantity of induced pluripotent stem cells (iPSCs), including the iPSCs in the presence of a GSK3 inhibitor (GSK3i) to form primitive streak (PS) cells, contacting the PS cells with a vector encoding Brachyury, and expressing Brachyury in the PS cells, wherein expressing Brachyury in the PS cells induces formation of induced notochordal cells (iNCs). In other embodiments, the iPSCs are cultured in the presence of about 1, 2, 3, 4, 5, 6, 7, 8, 9, or 10 μM of GSK3i. In other embodiments, the iPSCs are cultured in the presence of about 4, 5, or 6 μM of GSK3i In other embodiments, the iPSCs are cultured in the presence of GSK3i for 1, 2, 3, 4, 5, 6, 7, or 8 days. In other embodiments, the iPSCs are cultured in the presence of GSK3i for 3, 4, or 5 days. In other embodiments, the iPSCs are cultured in the presence of GSK3i for about 3 days. In other embodiments, the vector is pCMV6-AC-GFP vector. In other embodiments, contacting the PS cells with a vector comprises nucleofection. In other embodiments, contacting the PS cells with a vector comprises transfection. In other embodiments, expressing Brachyury in the PS cells comprises culturing the PS cells in A-RPMI media. In other embodiments, culturing the PS cells in A-RPMI media is for about 5, 6, or 7 or more days. In other embodiments, the methods includes exogenous addition of one or more of FGF, Noggin, and dickkopf 1 (DKK1) to the Brachyury expressing PS cells. In various embodiments, the iNCs are greater than about μm in size.

Also described herein is a composition of induced notochordal cells (iNCs). In other embodiments, the iNCs express one or more markers Galectin 3, chondroitin sulfate epitopes (3B3, 7D4, 4C3), Vimentin, Noggin, Integrins (a1, b1, a5, a6), and Brachyury. In other embodiments, the iNCs express one or more markers homeobox MIXL1, Brachyury, Noggin, Keratin 8 and Keratin 19. In various embodiments, the iNCs are greater than about μm in size.

Example 1

Characterization of the iNC Molecular Imprint and Comparison with Human NCs iNCs are derived from human iPSCs using the new method (FIG. 10). Transcriptomic and proteomic analyses are performed on iNCs and human NCs to fullydefine the similarities and differences between these two phenotypes.

Although extensively studied previously, NCs have no consensus marker genes that can fully identify the new iPSC-derived entity as canonical notochordal cells. To ensure correct cell differentiation, it is necessary to know the phenotype of NCs, the target cell population. Although there are few known markers of NCs, a full phenotypic profile of human NCs, a prerequisite for characterizing the phenotype of iPSC-derived NCs, has not been undertaken. For comparison the Inventors have access to young fresh cadaver spines through the National Disease Research Interchange (NDRI) protocol.

The isolation of notochordal cell candidates from the nucleus pulposus has been described in the literature (FIG. 1A,B). Successful RNA extraction from both cell types (small NP and large NC cells). Furthermore, both phenotypes could be distinguished using a limited range of known NC markers, including Keratin 8, Brachyury, and Noggin (FIG. 1C).

Figure 3B:
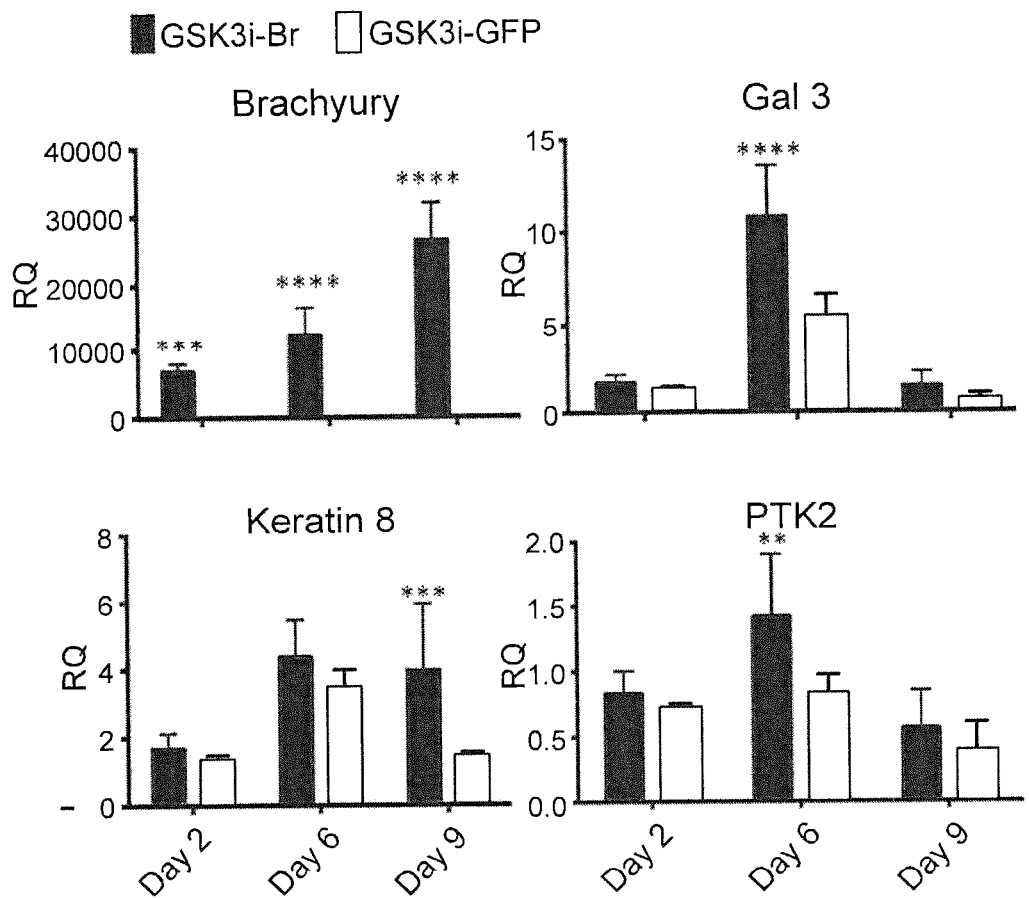
FIG. 3. Step 2—Differentiation of PS cells into iNC progenitor cells.

Previously published studies and data shown herein (FIG. 2) establish the feasibility of differentiation of iPSCs into primitive streak (PS) cells using short-term exposure to GSK3i. Once iPSCs are exposed to GSK3i, they rapidly change their morphological structure and start expressing PS markers (MIXL1 and Brachyury) and notochordal markers (Keratins 8, 19; FIG. 2C). Among the PS markers, Brachyury (T-box) transcription factor expression is the highest and has been identified as a major factor involved in notochord development during embryogenesis. The Inventors' preliminary data indicate that overexpression of Brachyury using non-viral transfection of PS cells leads to an NC cell—like phenotype (as shown by expression of several NC markers in FIG. 3).

Example 2

Human NC Isolation and Culture

Human NC isolation: In the proposed study, one can implement an NC cell isolation procedure based on cell size (FIG. 1). Young human cadaver spines are acquired (n=5, age at time of death 0-18 years). NP tissue is dissected in aseptic conditions, and the NPs are enzymatically digested overnight with 0.25% collagenase and 1% hyaluronidase. Cells are washed with PBS, and clusters of NCs are separated from the small NP cells using a 70-μm cell strainer (see FIG. 1), as previously reported by others.

Example 3

Reprogramming and Culturing iPSCs

Human iPSCs were prepared by reprogramming healthy human fibroblasts, nucleofected with episomal plasmid vectors as previously reported. The iPSC lines are expanded on Matrigel® matrix-coated plates (BD Biosciences, San Jose, Calif.) and chemically defined mTeSR™1 media (StemCell Technologies Inc., Vancouver, BC, Canada).

Example 4

Derivation of iNCs from iPSCs

Figure 4A:
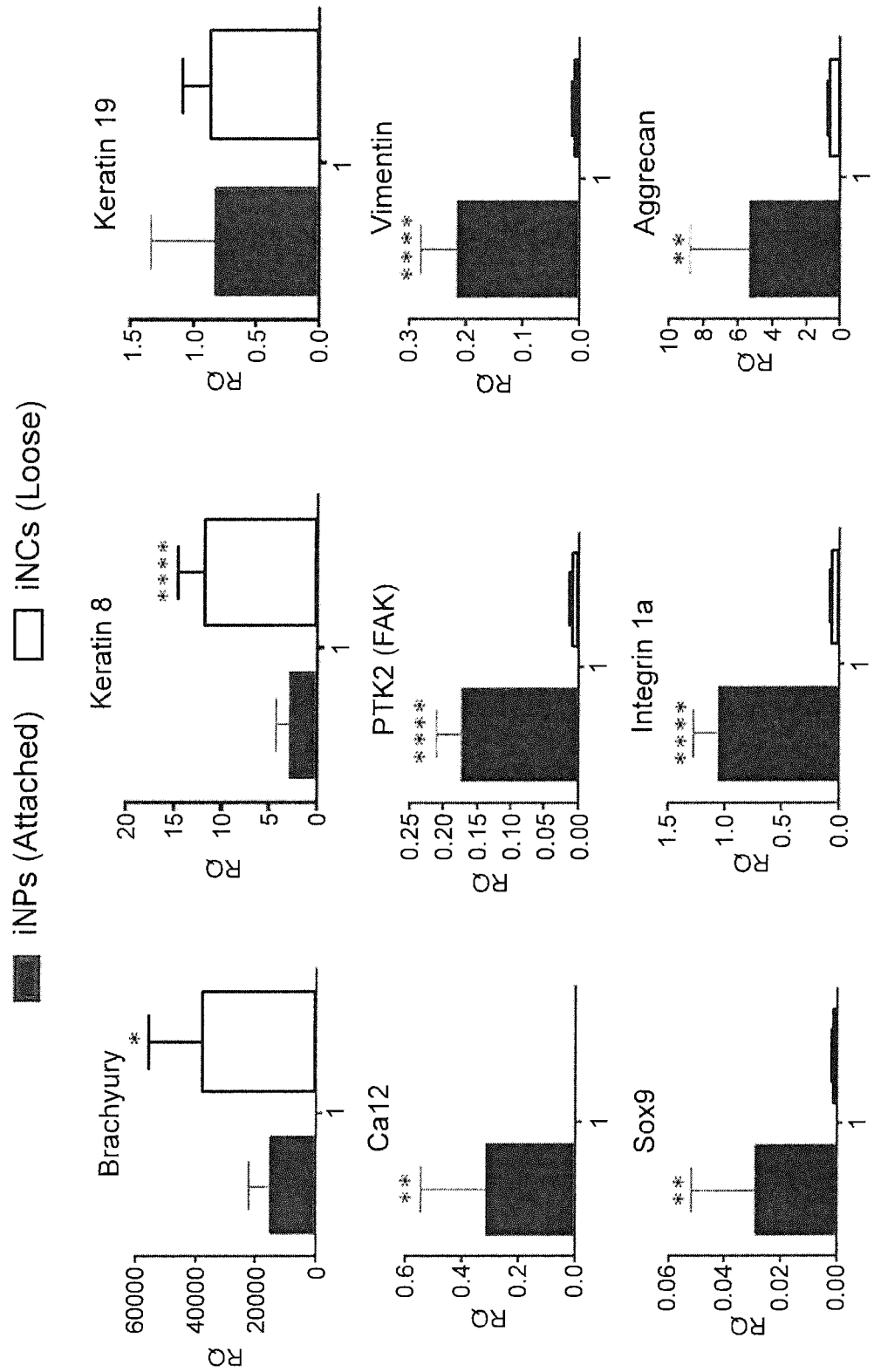
(FIG. 4A) The upper layer of cells could be easily separated from the lower level of cells, and therefore we could analyze them separately. Gene expression analysis on Day 6 after Brachyury nucleofection showed a higher expression of notochordal marker genes (Brachyury, Keratins 8 and 19) in iNCs than in iNPs. In contrast, the iNP population displayed a higher expression of chondrogenic markers (Aggrecan, Sox9), NP markers (PTK2, CA12), and MSCs markers that are not only expressed in MSCs, but also in notochordal cells (Vimentin, Integrin 1a). Bars indicate SEs, *p<0.05; p<0.01; *p<0.001; ****p<0.0001.
Figure 4B:
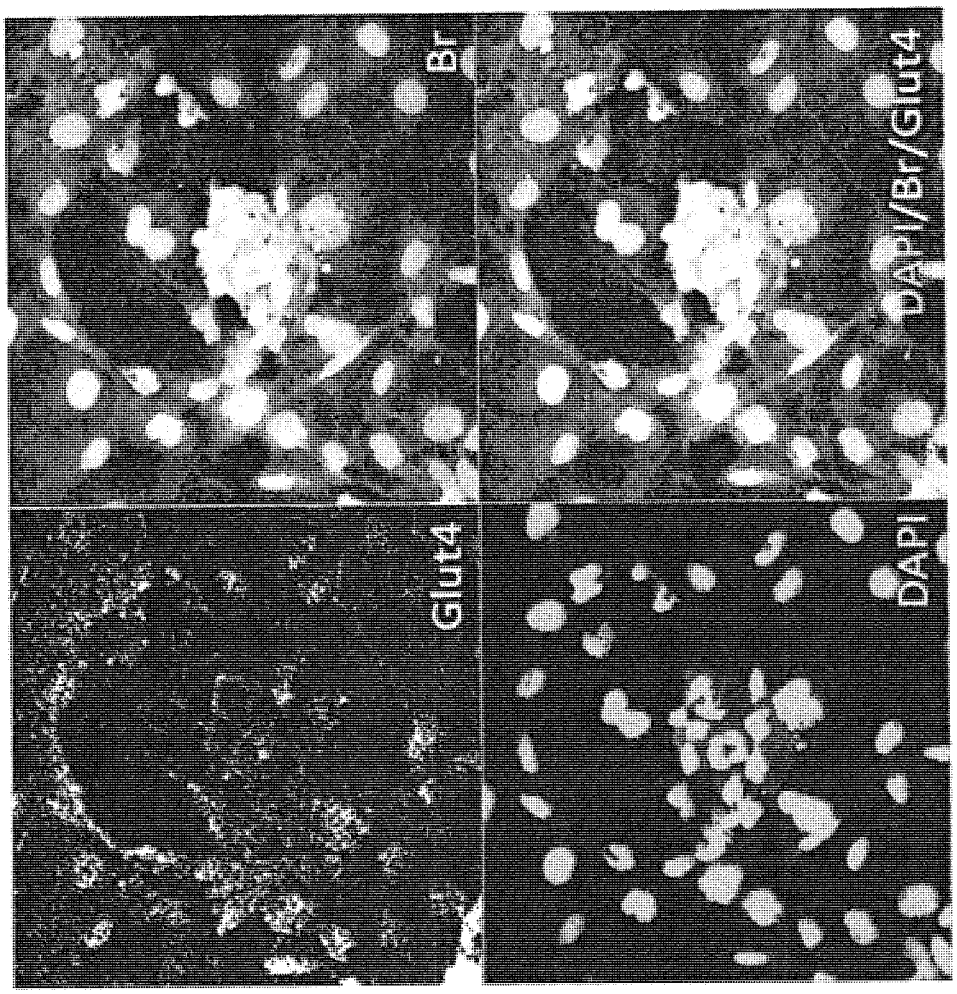

Derivation of iNCs from iPSCs is performed using a previously established two-step protocol. During Step 1, the iPSCs are differentiated into PS cells via a 4-day exposure to 504 GSK3 inhibitor (Millipore, Billerica, Mass.) (FIG. 2). During Step 2, after GSK3i treatment, the cells are nucleofected with human Brachyury-encoding pCMV6-AC-GFP vector plasmid (OriGene, Rockville, Md.). Cells are cultured for 6 days in A-RPMI media; then we can distinguish two cell types (as shown in FIG. 4) and harvest cells for transcriptomic and proteomic analyses.

A transcriptomic analysis of iNCs and human NCs is performed to examine similarities and differences between the two phenotypes (n=5). Transcriptomic profiling is performed using Illumina RNA-Seq technology on the MiSeq platform.

In addition to the whole transcriptome, small RNAs (miRNAs, snoRNAs) are analyzed to identify transcript isoforms unique to NCs. Downstream validation of the identified target genes/small RNAs are performed using quantitative real-time PCR (qPCR) via ABI7500 Prism (Applied Biosystems, Foster City, Calif.) and TaqMan® expression assays. Further validation of the few identified genes are done at the protein level by performing immunohistochemistry (IHC), immunofluorescence (IF), and/or flow cytometry, as appropriate.

Example 5

Proteomic Analysis

In addition to transcriptome profiling, one can compare protein expression profiles of iNCs and hNCs (n=5). To compare the proteomes of both cell types, isobaric tagging of each sample (iTRAQ) is followed by pooling of the tagged samples and analysis by 2-dimensional liquid chromatography and tandem mass spectrometry (2D-LC-MS/MS). iTRAQ has significant advantages over other protein profiling methods, since the isobaric nature of the tag ensures that signals from all samples are summed as part of the analysis, resulting in an increase in signal for each peptide and allowing deeper penetration into the proteome.

Processed transcriptome and proteome data can be further studied by performing an Ingenuity pathway analysis to define key processes that differ between the two cell populations. By applying Expression2kinases software, one can predict key regulatory transcription factors and signaling events that are specific to iNCs.

Example 6

Elucidating the Influence of NP-Simulating Mechanical Loading Conditions on iNCs and the Cell Response The primary role of NCs is to support the nucleus pulposus matrix, and thus these cells are the main effectors in restoring the environment, NP cells, and a proteoglycan-rich matrix in cases of degeneration. So far the functionality of NCs has not been tested in conditions that closely resemble the unique environments of degenerate and healthy IVDs. The 3D structure of the nucleus pulposus, biomechanical forces (mostly compression), low oxygen levels, and slow nutrient exchange due to a lack of blood supply are the most important factors that compose this environment.

By studying iNC gene expression and functionality in an in vitro microenvironment one can establish a platform that resembles in vivo conditions. Therefore, cells are embedded in 3D PuraMatrix® peptide hydrogel, which has been successfully used in several cartilage repair and IVD cell therapy models, following which the cells are stimulated by mechanical compression using the FlexCell® FX-5000 system (FlexCell Corp, Burlington, N.C.).

Figure 5:
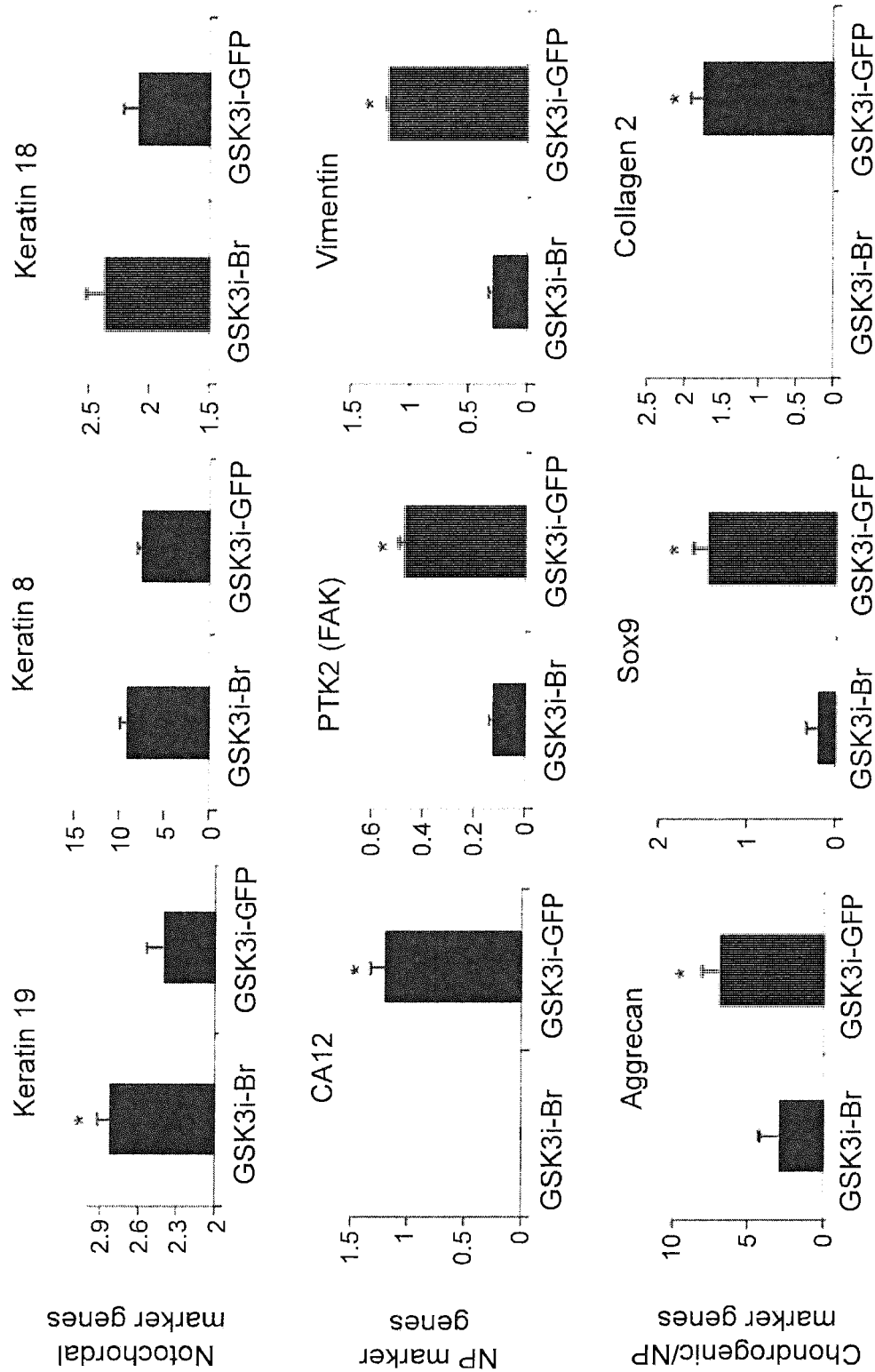
FIG. 5. iNCs sustain notochordal phenotype in NP differentiation conditions in vitro. PS cells were nucleofected either with Brachyury-encoding plasmid or GFP reporter gene, encapsulated in hydrogel, and cultured in NP-differentiation conditions (NP media and hypoxia) for 21 days. RNA was extracted, and the gene expression profile was evaluated using qRT-PCR for NC and NP markers. Gene expression analysis showed that the NP markers CA12, PTK2, and Vimentin as well as the chondrogenic markers Aggrecan, Sox9 and Co12, were downregulated, and that the NC markers Keratins 8, 18, and 19 were upregulated or did not change in Brachyury-overexpressing cells, compared to GFP-expressing cells. This indicates that NP differentiation conditions affected PS-GFP cells but not PS-Br cells, which sustained their NC phenotype. Bars indicate SEs, $*p<0.05$.

In the Inventors' preliminary study, iNCs embedded in PuraMatrix® peptide hydrogel sustained their viability and phenotype under NP differentiation conditions (FIG. 5). Furthermore, cell responses to mechanical loading in this setup have been intensively analyzed. In preliminary studies, iNCs embedded in PuraMatrix® peptide hydrogel displayed downregulation of NP markers in response to compression strain (FIG. 6), indicating the feasibility of a cell response to overloading in vitro.

Example 7 iNCs in IVD-Mimicking Environmental Conditions

A functional phenotypic characterization of iNCs and a comparison with hNCs are conducted in an IVD-like environment in vitro. One may compare two cell populations—iNCs and hNCs ($10^6$ cells per construct, n=3)—each encapsulated in PuraMatrix® peptide hydrogel (Corning, Tewksbury, Mass.). The cell constructs are placed in 6.5-mm-diameter Costar® Transwell® cell culture inserts (Corning) and cultured under hypoxic conditions (2% O2) for up to 28 days in NP differentiation medium (DMEM/F-12 with 15 mM HEPES, L-glutamine, and pyridoxine hydrochloride (1:1, v/v; Life Technologies) with additional L-ascorbic acid-2-phosphate, non-essential amino acids, insulin-transferrin-selenium (ITS), and penicillin-streptomycin (all from Life Technologies), as was done in preliminary studies (FIG. 6) and previously described. The media is changed every 3-4 days. To simulate a low mechanical load on IVDs, the iNC-PuraMatrix® peptide hydrogel constructs are stimulated by intermittent loading—1 h (30 min twice per day) at 10% compression and 1 Hz—since these parameters have been shown to enhance bioengineering of an IVD ex vivo and found to be ideal for the investigation of 3D chondrocyte-seeded constructs in a compression bioreactor. To simulate mechanical overloading, iNC constructs are stimulated by a different intermittent loading—1 h (30 min twice per day) at 30% compression and 1 Hz—since an amplitude of 30% strain has been demonstrated to have detrimental effects on cell viability and function in bovine cartilage explants.

Example 8

Cell Survival and Proliferation

To assess cell viability in PuraMatrix® hydrogels (n=5 per time point, per study group), constructs are stained on Days 2, 7, and 14 by using a LIVE/DEAD staining kit (Molecular Probes) according to the manufacturer's protocol. Controls for the LIVE/DEAD assay can be prepared by the addition of 70% ethanol for 30 min to cell-seeded hydrogels yielding 100% red staining, which is indicative of cell death. LIVE/DEAD images are captured using a Zeiss 780 confocal microscope. Five representative 40× magnification images for each time point in each study group is evaluated. The number of live cells within each image is counted. To assess proliferation, one can evaluate cell numbers based on ATP content by performing a CellTiter-Glo™ (Cat. no. G7572; Promega, Madison, Wis.) luminescent cell viability assay, as described previously. Cell numbers on Days 1, 3, 7, and 14 post-seeding and calculate relative light units are plotted against a standard curve of known cell numbers and proliferation rate.

Example 9

Gene Expression Analysis

RNA is be extracted from the cell constructs using an RNeasy® Mini kit (Qiagen, Valencia, Calif.) and reverse transcribed using random primers and reverse transcriptase (Promega Corp., Madison, Wis.). Responses of cells to two compression conditions are tested by detecting gene expression of the NC markers Keratins 8 and 18, Galectin 3, and Integrins a1 and Noggin, and the NP markers CA12, PTK2, Glut1, Versican, Aggrecan, Sox9, and Pax1.10. One can also determine gene expression of markers reported to be expressed in both cell types, namely, Keratin 19, Vimentin, CD24, Shh, and Co12. Additionally, one can examine the expression of genes found to be specific to NC cells. Quantitative PCR is performed using an ABI 7300 Prism and TaqMan® expression assays.

Example 10

Matrix Composition

Matrix composition is evaluated in response to loading conditions by performing a DMMB assay to determine the amount of secreted glycosaminoglycans (GAGs), as published earlier. For this purpose, hydrogels are harvested after 21 days. In brief, implants are digested using Proteinase K. DMMB dye is added and read at 525 nm with the aid of a spectrophotometer. Results are obtained by using a standard curve of chondroitin sulfate.

To quantify collagens, samples are hydrolyzed in 0.5M acetic acid for 18 h at 4° C. The acid extracts are reacted with Sircol® reagent, and collagen-bound dye is quantitated according to the manufacturer's protocol. Collagen is estimated by measuring the amount of hydroxyproline, assuming 13.4% (w/w) hydroxyproline content in collagen, as reported elsewhere. The GAG/hydroxyproline ratio indicates resemblances of differentiated constructs to NP or cartilage. Additionally, the constructs are fixed in formalin and embedded in paraffin to proceed and validate the formation of Aggrecan and Collagen II. Histological sections are subjected to immunofluorescence staining with specific antibodies against the NP matrix—abundant proteins Aggrecan and Collagen II and the NC markers Keratin 8 and Keratin 18, as reported earlier.

Example 11

Expected Results and Alternative Approach

Preliminary data (FIGS. 1-5) suggests that the iPS-derived notochordal cells resemble human NCs in phenotype. Of interest is confirming both a phenotype and molecular imprint of iNCs. By establishing a protocol to differentiate iPSC into iNCs, the generated iNCs allow for a comparison with native human NCs for comparison of their status as bona fide NCs. One can identify specific marker genes that can be incorporated into the list of genes commonly identified with notochordal cells by working with human native NCs. One does not anticipate a high donor-to-donor variation, because the cadaveric donors are young (0-18 years). In case such variability does exist, one can separate donors into 0-9 and 10-18 year age groups. Importantly, using the described methods, one can develop iNC phenotype closer towards that of hNCs, by altering the differentiation process following Brachyury overexpression. This includes, for example, optimized short-term treatment with additional factors such as FGF, Noggin, and DKK1. PuraMatrix® peptide hydrogel, previously used in several cartilage and IVD tissue engineering applications, has advantages for in vivo application because it is an injectable, synthetic hydrogel. However, if this additives does not provide the optimal elasticity needed to promote NP matrix formation in the in vitro studies, other materials such as Fibrinogen-Tetronic-1307 1 KPa (TF) hydrogel can be used, as reported to promote chondrogenic and NP differentiation.

Example 12

Elucidating the Beneficial Effect of iNCs on NP Cells, Derived from Healthy and Degenerate IVDs, in Conditions that Mimic IVD Degeneration In Vitro It has been shown that NCs play a fundamental role in disc integrity via protection of NPCs and promotion of matrix deposition by NPCs. It was also shown that NPCs have a limited regeneration capacity at onset of degeneration. Therefore, it is suggested that that iNCs are able to activate NPCs in degenerate discs. The beneficial regulatory effect of iNCs on NPCs in normal and degenerative states should demonstrate iNCs' ability to activate NPCs to secrete matrix proteoglycans and rebuild NP tissue. iNCs are compared with native human NCs in their ability to induce activation of NPCs, resulting in extended proliferation, and in synthesis of a proteoglycan-rich matrix. This effect is tested using NPCs isolated from both healthy and degenerate discs (HNPCs and DNPCs, respectively), under compression mechanical loading conditions, since HNPCs and DNPCs are expected to respond differently to differentiation stimuli.

Example 13

Porcine IVD Degeneration

Porcine IVD degeneration is induced using a previously published annular injury method at three spine levels (L2-5).

Pigs are used to obtain the desirable amount of cells from healthy and degenerate NP. Following the annular injury the disc degeneration process is monitored using MRI, and once degeneration occurs (6-8 weeks postsurgery) the pigs are euthanized and 3 degenerated discs along with 3 healthy discs are harvested. DNPCs and HNPCs are isolated and expanded in vitro. NCs are excluded using 70-μm cell strainers. Native human NCs are derived from human young cadaveric IVDs.

Example 14

Beneficial Regulatory Effect of iNCs

Beneficial regulatory effect of iNCs is assessed by using co-culture or co-encapsulation of iNCs or hNCs with NPCs from healthy or degenerated discs in hydrogels and by applying two biomechanical conditions: 1) low dynamic compression (simulating the healthy disc environment) using the FlexCell® system with 10% compression at 1 Hz twice daily for 30 min; and 2) high dynamic overloading (simulating the degenerated disc environment) using the FlexCell® system with 30% compression at 1 Hz twice daily for 30 min. The co-culture system includes 6 experimental groups (n=5): 2 groups with homogeneous HNPC and DNPC populations as negative controls (106 cells each) and 4 groups of different combinations of iNCs or hNCs and DNPs or HNPs (5×105 cells each). The human notochordal components of the co-culture (iNC and hNC) are labeled with CM-DiI Cell-Labeling Solution (Molecular Probes, Eugene, Oreg.) and the porcine NPCs are labeled with CM-DiO Cell-Labeling Solution, so that the cells are distinguished in paraffin sections and IF analysis. Cell proliferation and viability is determined similarly to what was described using LIVE/DEAD staining and the CellTiter-Glo™ assay.

TABLE 2

Cell Counting

| Cell Type | Group I | Group II | Group III | Group IV | Group V | Group VI |
|---|---|---|---|---|---|---|
| Hydrogel | + | + | + | + | + | + |
| hNC-DiI | – | – | 50% | 50% | – | – |
| iNC-DiI | – | – | – | – | 50% | 50% |
| HNPC-iO | 100% | – | 50% | – | 50% | – |
| DNPC-iO | – | 100% | – | 50% | – | 50% |

Example 15

Beneficial Regulatory Effect of iNCs

The contribution of iNCs to IVD regeneration is tested using qPCR specific primers for human and porcine marker genes. The construct is harvested after 21 days in culture in IVD-mimicking conditions in vitro (2% O2, 3 different mechanical loading conditions, NP media). The RNA is extracted and reverse transcribed. Quantitative PCR is performed using an ABI 7300 Prism (Applied Biosystems, Foster City, Calif.) and TaqMan® expression assays for the NC marker genes Keratins 8 and 18, Galectin 3, and Noggin, and the NP markers CA12, PTK2, Glut1, Versican, Aggrecan, Sox9, and Pax1, according to the manufacturer's protocol. One can also check gene expression of markers that are expressed in both cell types: Keratin 19, Vimentin, CD24, Shh, and Col2.

Example 16

Histological and Immunofluorescence Analyses

Three constructs from each group are subjected to fixation, paraffin sectioning, and histological analysis. Paraffin slides are stained for H&E and Alcian blue standard stains for morphological evaluation. Then the slides will receive immunofluorescent staining against the human NC markers Galectin 3, chondroitin sulfate epitopes (3B3, 7D4, 4C3), Vimentin, Noggin, Integrins (a1, b1, a5, a6), and Brachyury, as well as the describe panel of NC markers. In parallel, on the same slides, one can use primary antibodies against the porcine NP markers Aggrecan, CA12, Versican, PTK2, Glut1, Col2, Sox9, and Pax1 in a paired manner. This way one can identify cells labeled with fluorescent dyes (CM-DiI and CM-DiO) and determine which cells express particular NC or NP markers.

For matrix composition evaluation, the properties of the matrix secreted by each group and cell combination is evaluated according to total GAGs (DMMB assay) and the GAG/collagen ratio (hydroxyproline quantitative assay). Additionally, one can measure the quantity of HIF1a protein in the cell construct by using Western blot analysis and will thus define the resemblance of the constructs to NP tissue.

Figure 6:
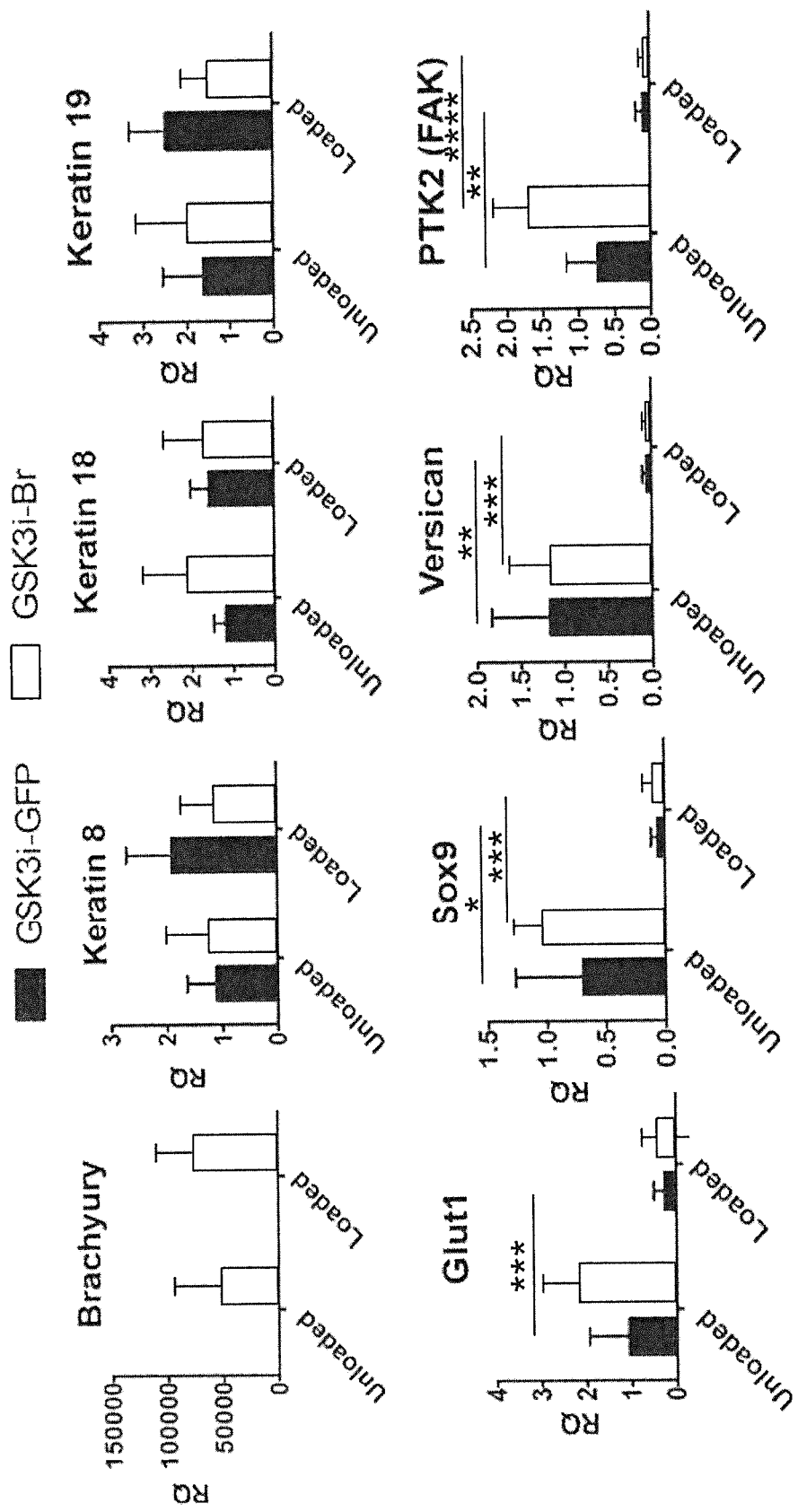
FIG. 6. Effect of dynamic overloading on NP marker gene expression. PS cells were nucleofected with either Brachyury- or GFP-encoding plasmids and on Day 6 of culture were encapsulated in fibrin gel. The constructs were placed in the FlexCell®system and exposed to dynamic compression-20% compression at 1 Hz for 2 hours, twice per day for 48 hours. Afterward, the constructs were harvested and RNA was extracted. Gene expression analysis showed that the loading conditions resulted in downregulation of NP markers in both types of cells, but not downregulation of notochordal markers. Bars indicate SEs, $*p<0.05$; $p<0.01$; $*p<0.001$; $****p<0.0001$ (comparison of loaded and unloaded groups).
Figure 7:
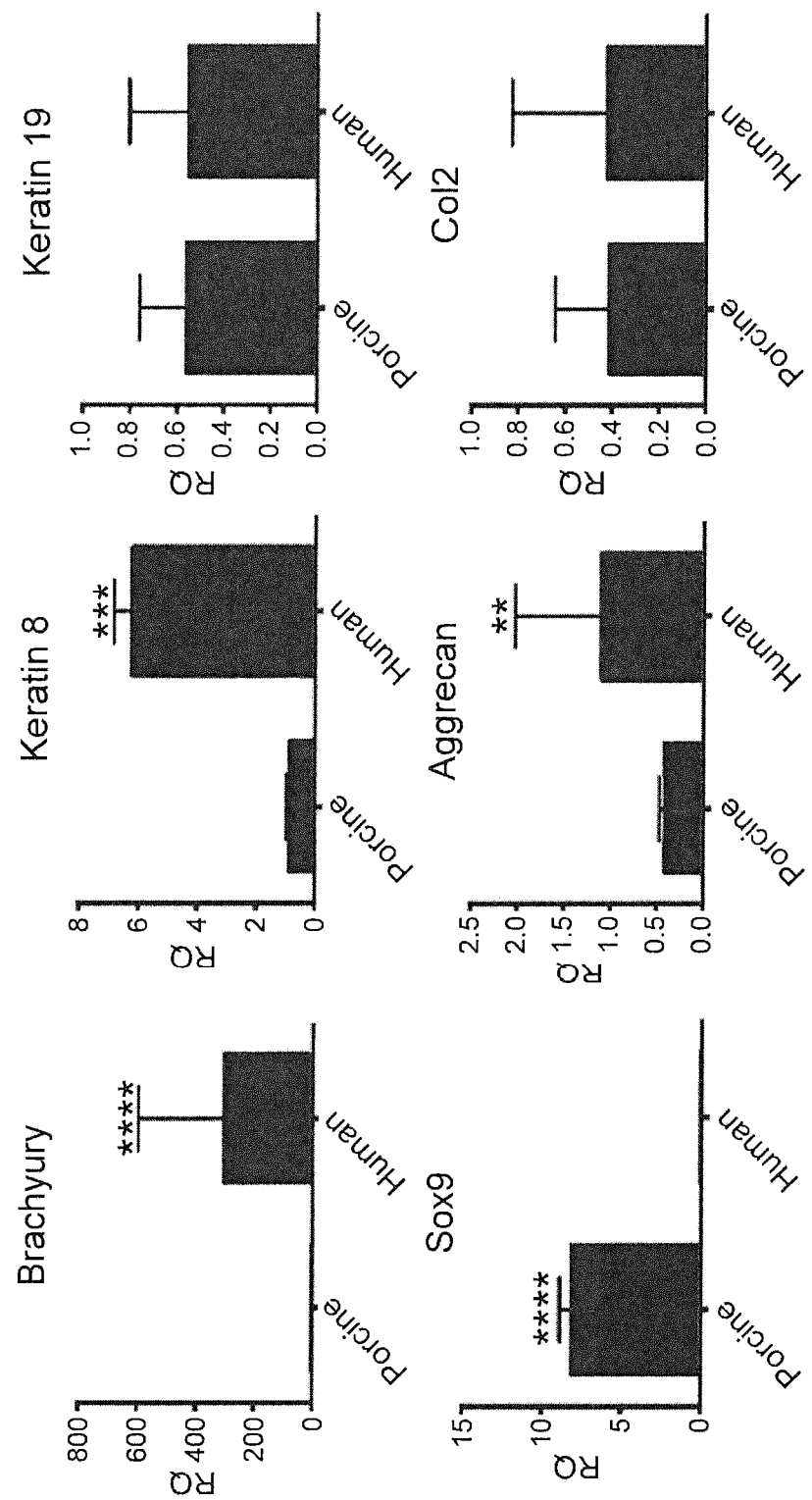
FIG. 7. Co-culture of iNCs with HNPCs: gene expression. iNCs were generated using the protocol described above. NPCs were isolated from porcine healthy NPs. Both cell types were encapsulated in PuraMatrix® peptide hydrogel in a 1:1 ratio and cultured in NP differentiation conditions. On Day 21 the constructs were harvested and RNA was extracted. Gene expression analysis was performed using human and porcine specific primers for NC/NP marker genes. The results show that human cells expressed higher levels of Brachyury, Noggin and Aggrecan, whereas porcine cells expressed higher levels of Sox9 and similar levels of Keratin 8 and Co12, indicating that there were more notochordal cells of human origin and more NP-like cells of porcine origin. Bars indicate SEs, $*p<0.05$; $p<0.01$; $*p<0.001$; $****p<0.0001$.

It is suggested that notochordal cells will have a significant beneficiary effect on NP cells that can be recapitulated with iNCs on NP cells. Here, it is anticipated that a co-culture of iNC with NPCs will have a synergistic effect due to the regulatory role NC cells play in disc formation and young spines. Preliminary results showed high survival of cells and expression of NC markers (FIG. 6). Mechanical loading of cell constructs may be challenging in fine-tuning between low and high loading conditions. If mechanical loading of the cells does not achieve the effect expected, one can further optimize the mechanical loading conditions and the ratio of co-cultured cells. If the NPCs do not respond to iNCs signals, one can use human MSCs for the co-culture studies.

Example 17

Evaluation of the Regenerative Potential of iNCs in a Large Animal Model of IVD Degeneration Ultimately, a key goal for therapeutic development is to assess the engraftment, survival, and differentiation potential of human iNCs in a porcine model of disc degeneration in vivo. The Inventors previously established a large animal model for disc degeneration that resembles in size the human IVD. Not only are there implications of scaling with small versus large disc volume, but also some animals may be inappropriate as the procedure proposed is physically challenging in small species. In small quadrupeds, such as rabbit, mouse, or rat, much lower forces are applied than in humans. Biochemical composition of the disc differs between species, and IVDs in large quadrupeds more closely resemble discs in humans than those in small animals.

Figure 8:
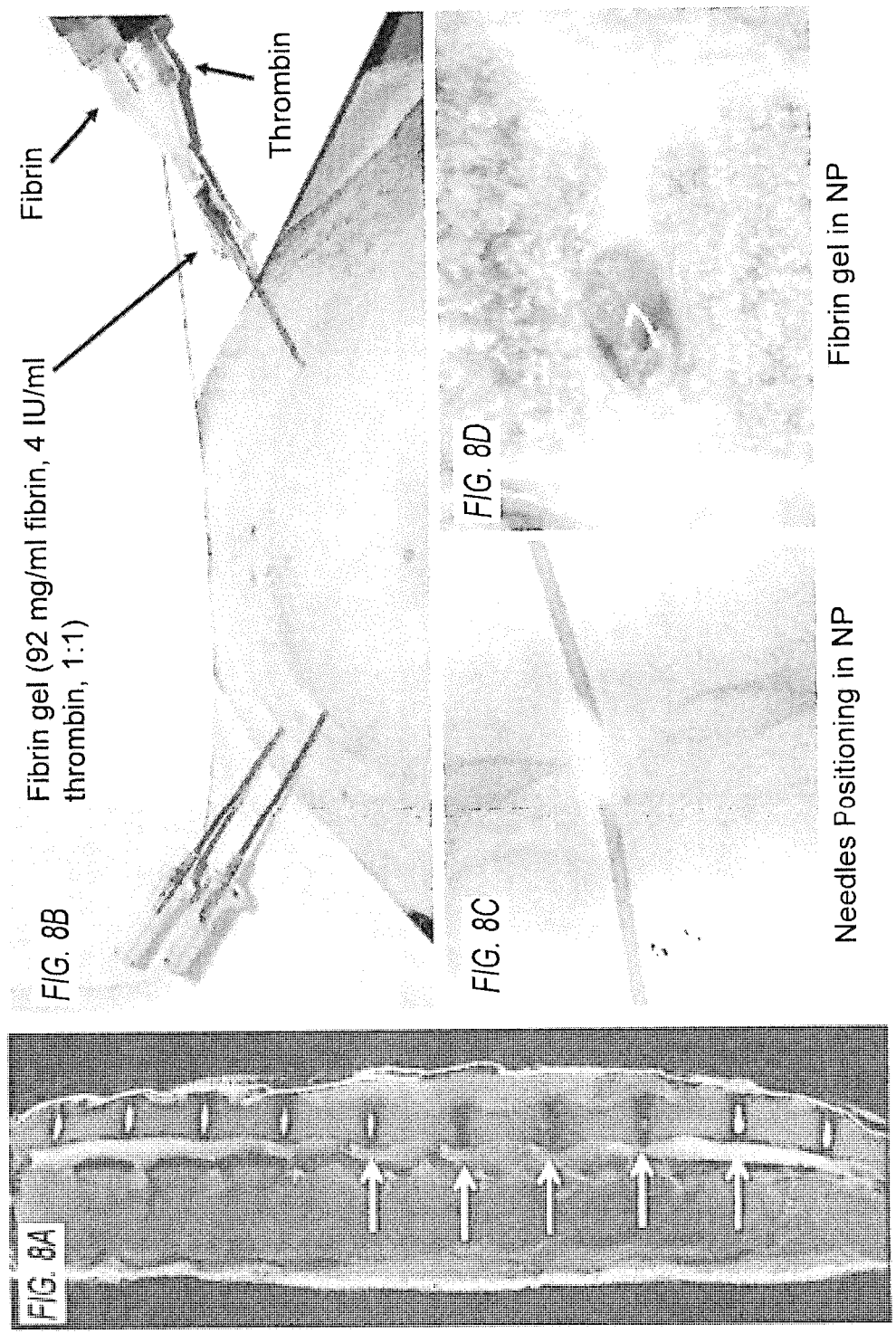
FIG. 8. Porcine IVD model.
Figure 9:
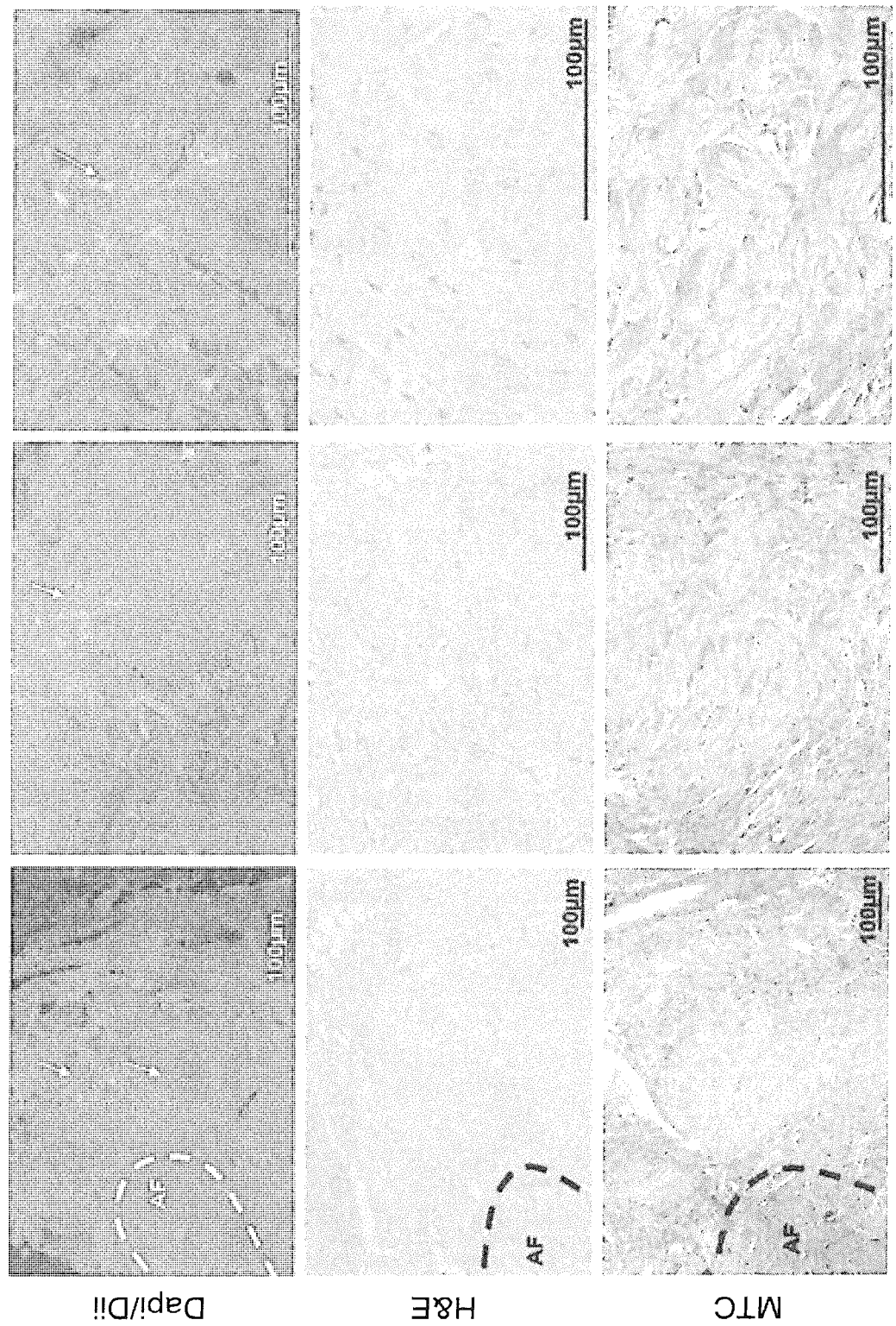
FIG. 9. DiI-labeled MSCs detected in rodent IVD—engraftment and differentiation. Human DiI-labeled MSCs were injected into rat IVDs. The discs were harvested, sectioned, and stained with H&E and MTC. Engrafted MSCs were detected inside the disc using light and fluorescence microscopy. Chondrogenic lineage differentiation was observed and is depicted by MTC staining.

Degeneration and regeneration processes can be monitored using MRI. The Inventors have previously shown the feasibility of MSC injection and survival inside IVDs (FIGS. 8, 9). The Inventors' previous study showed that annular injury—induced degeneration affects the phenotype of NP-residing cells, and thus it is suggested that addition of cells with the NC phenotype would rejuvenate the disc and activate resident cells for regeneration and repopulation of the disc. The IVD is an immuno-privileged organ that can be treated with xenogeneic human cells without risk of rejection. Here, validation of in vitro studies can be translated into a clinically relevant in vivo model of disc degeneration.

Example 18

Methodology

For IVD degeneration model, twenty-four healthy female Yucatan miniature pigs with an average age of 10 months and weights ranging from ~40 to 60 kg are included in large animal study. NP degeneration is induced in conditions of general anesthesia via a posterolateral approach at targeted levels (L2-3, L3-4 and L4-5) by a superficial 4-mm-deep stab incision made with a surgical scalpel (#10 blade) through the AF into the center of the NP and parallel to the endplate, as previously reported. Seven to eight weeks later, the animals are imaged with MRI (Siemens Medical Solutions USA, Inc., PA) and disc heights measured to verify degeneration.

For IVD regeneration in vivo, each degenerated disc is treated differently (see Diagram 3). One will serve as a control and be injected with hydrogel only (1 ml). The second one is injected with $2\times10^6$ iNCs pre-labeled with CM-DiI fluorescent dye and encapsulated in hydrogel. The third disc is injected with 2×106 hNCs pre-labeled with CM-DiI as a positive control.

For IVD imaging, the regeneration process is monitored by MRI every 4 weeks postinjection up to Week 12 (up to 3 times), similar to monitoring in previous studies involving the porcine IVD degeneration model. Disc height and water content are quantitatively evaluated. At Week 12 or earlier, if regeneration of the disc is evident, the pigs are euthanized and the discs harvested. Imaging data and cell engraftment, proliferation, and differentiation is assessed to evaluate the efficiency of the regeneration.

Example 19

Additional Study Parameters

Cell engraftment, survival, and differentiation. After harvesting, NPs are digested enzymatically (n=6) and the cellular components of the NP is evaluated using flow cytometry. Host (porcine) NPCs as opposed to donor iNCs, or hNCs are differentiated using fluorescence labeling (CM-DiI). Additionally, mesenchymal (CD44, CD29, and CD90) and NP (CD24, Glut1) surface marker expression is assessed by flow cytometry.

For, matrix deposition, GAGs are quantified in each NP group by using the DMMB assay (n=6) and collagens by using the hydroxyproline assay (n=6). The GAG/collagen ratio is calculated as described.

For gene expression analysis, another group of NPs (n=6) is used for gene expression analyses of notochordal and NP markers. The discs are harvested and homogenized. RNA is extracted, and NC and NP marker panels assessed using qPCR.

For histological and immunofluorescence analyses, another group of animals are used to qualitatively evaluate the morphological structure, matrix composition, and iNC contribution to IVD regeneration (n=4). The disc is harvested, fixed in formalin, and subjected to histological analysis. Then immunofluorescent stains are applied to elucidate factors secreted by the host porcine cells and co-localization of matrix proteins (Aggrecan, Col2) with DiI-labeled donor (hNC or iNC) cells.

The Inventors anticipate seeing significant improvements in IVD water content and disc height (outcomes of regeneration) within 12 weeks after cell injection. If leakage of cells from the IVD is observed after injection, one can use tissue glue to seal the injection site. In case no improvement is evident, the animals are kept for up to 6 months, as previously reported and additional minimally invasive injections of cells are considered. NPCs from degenerate IVDs are less active; if there is no response to the iNC's signals, hMSCs are injected into the degenerated disc alone (as a control) or with the iNCs.

This design study should establish a molecular imprint of NCs generated from human iPSCs. The development of iNCs could provide a reproducible and inexhaustible source of human notochordal cells to treat DDD, which can be delivered in a minimally invasive manner to treat one cause of DDD, namely, exhaustion of the original NC population.

Example 20

Further Studies

As described, the Inventors developed a 2-step approach supporting a controllable differentiation process using a well-defined gene and a small molecule. This approach will be more acceptable for cGMP production and FDA approval, and thus having more potential to reach clinical application. iNCs will induce regeneration of a degenerate IVD. In developing a reliable step-by-step method to generate iNCs that will resemble human NCs in their phenotype and functional characteristics, the Inventors also examined their survival and regenerative potential in in vitro and in vivo models of IVD degeneration.

Figure 13A:
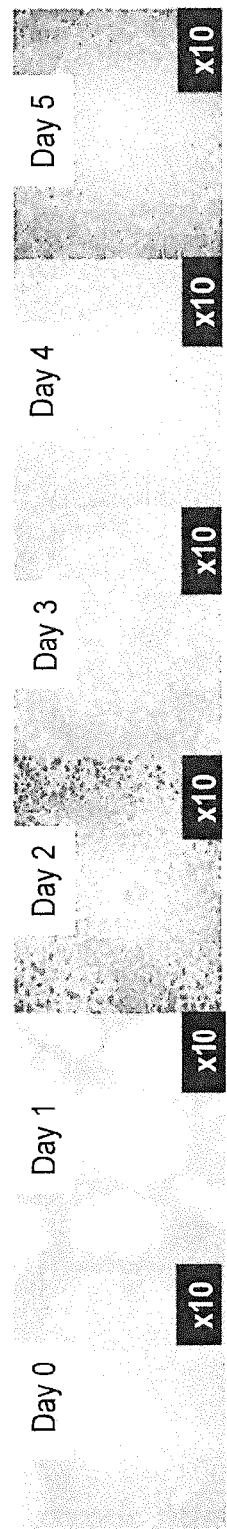
(FIG. 13A) Morphological changes during treatment were depicted with light microscopy.
Figure 13B:
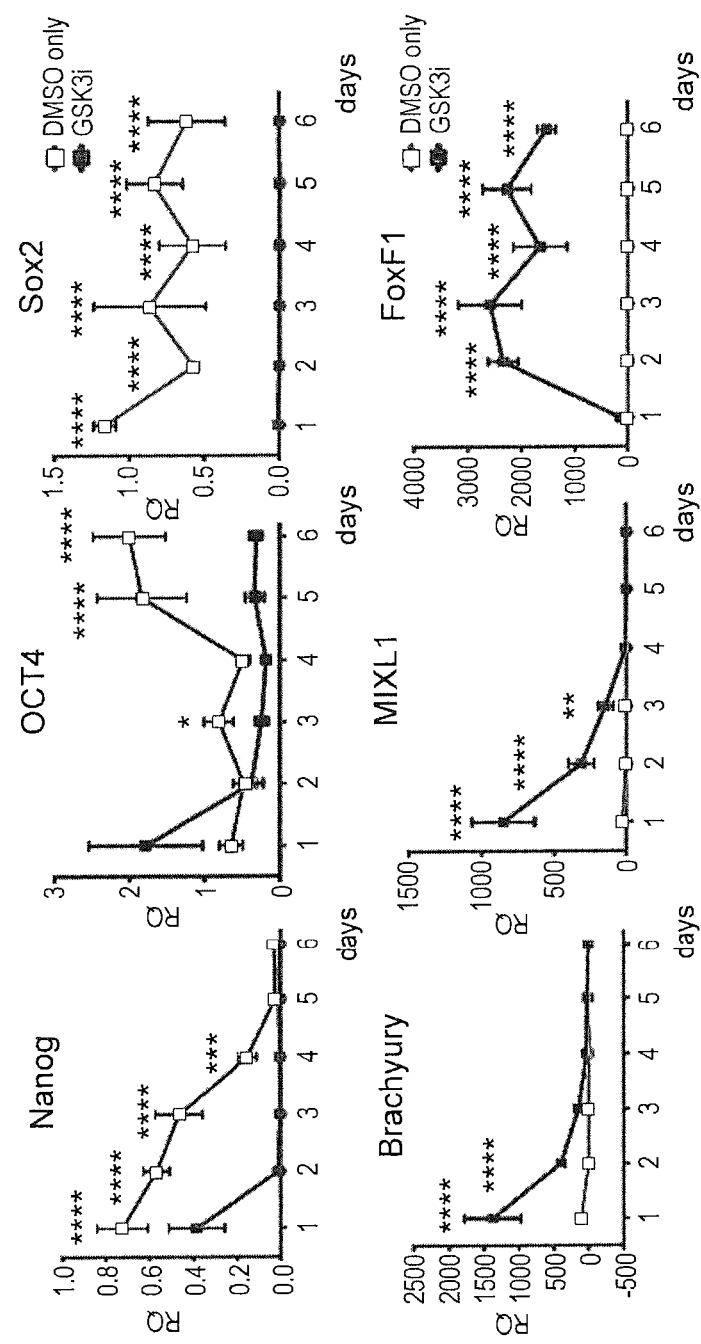
(FIG. 13B) Gene expression analysis of PS cells shows a rapid and significant decline in expression of pluripotency markers in GSK3i-treated cells compared to cells treated with vehicle only (DMSO). The mesodermal markers Brachyury and MIXL1 were upregulated 24 hours after addition of GSK3i to the media and their expression was significantly higher up to Days 2 and 3, respectively. An additional mesodermal marker, FoxF1, was upregulated after 48 hours of treatment and its expression remained higher than that in the DMSO group through Day 6. Results represent mean RQs calibrated relatively to untreated iPSCs (Day 0), n=6, bars indicate SEs, 2-way ANOVA with Bonferroni correction, $*p<0.05$; $p<0.01$; $*p<0.001$; $****p<0.0001$.

The Inventors isolated porcine cells residing in the nucleus pulposus, consisting of two populations: NP cells and NCs. There were two observable populations, "small" and "big" cells, expressing typical genes for each cell type, as seen in FIG. 1. These findings are consistent with those of previous studies and show that when separated by size, notochordal cells can be used as a positive control. Preliminary data (FIG. 13) demonstrated the feasibility of differentiation of iPSCs into primitive streak (PS) cells using short-term exposure to GSK3i (FIG. 13A). Once iPSCs are exposed to GSK3i, they rapidly change their morphology (FIG. 13B). GSK3i exposure decreased the expression of pluripotent markers, but induced expression of PS markers (MIXL1 and Brachyury), which declined in 2-3 days (FIG. 13D). FoxF1, another mesodermal marker, was upregulated after 2 days of GSK3i treatment and its expression was higher than that found in the control group until Day 6. Based on this experiment, the best timing to promote PS cell differentiation toward notochordal progenitors appears to be Day 3, when the pluripotent phenotype is lost, but the mesodermal phenotype is still detectable.

Example 21

Brachyury Supports Fate Specification Towards iNCs

Figure 14B:
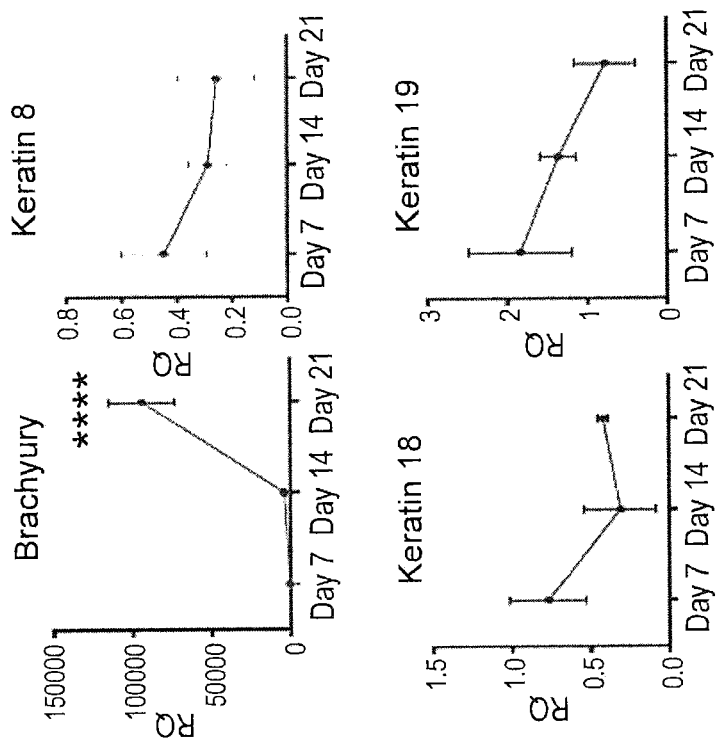
(FIG. 14B) Phenotype stability: iNCs in ABs were grown in hypoxic conditions and NC marker gene expression was analyzed once a week. Bars indicate SEs, $****p<0.0001$.
Figure 14A:
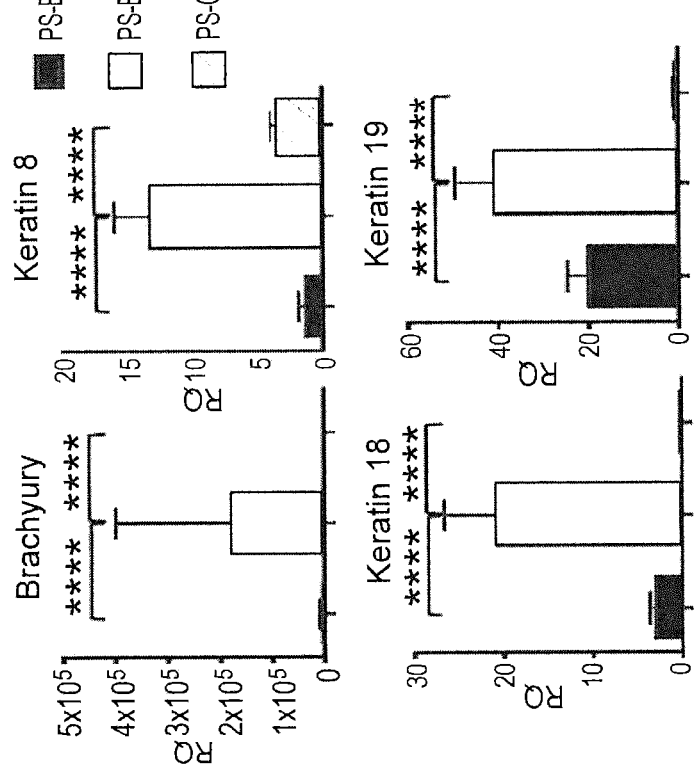
(FIG. 14A) PS cells were nucleofected with either Brachyury (Br) or GFP-encoding plasmids and cultured in A-RPMI in vitro for 3 days. Afterward, they were either grown in vitro for 7 days (2D) or in 3D alginate beads (ABs). Differentiation towards notochordal cells was evaluated using gene expression for NC marker genes.

Among the PS markers, Brachyury (T-box) transcription factor has been identified as a major factor involved in notochord development during embryogenesis. As the second step of differentiation Brachyury was overexpressed in PS cells using nonviral transfection, leading to an NC progenitor phenotype (as shown by expression of several NC markers in FIG. 14).

Figure 15:
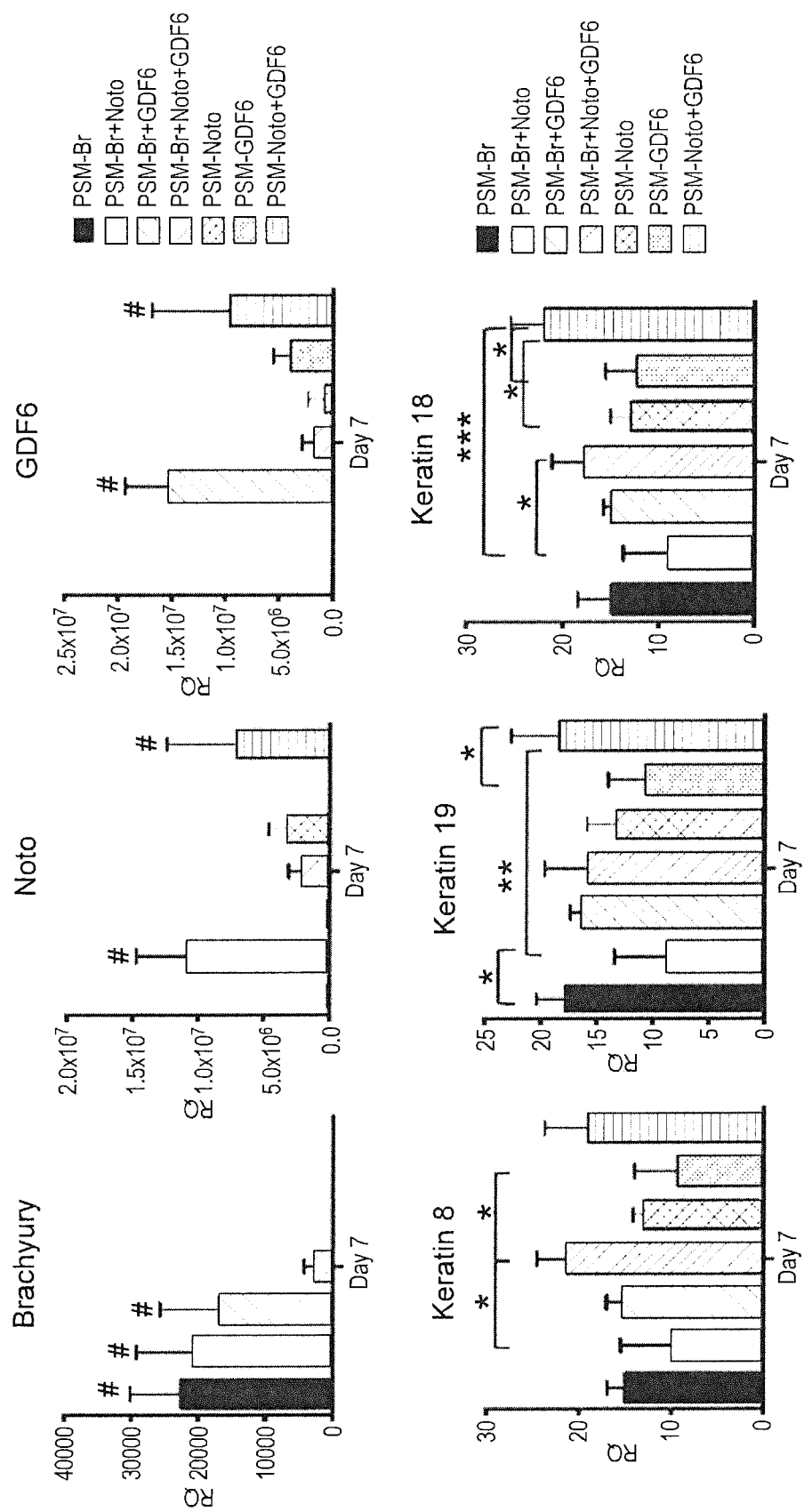
FIG. 15. Step 2—Optimization with additional factors. The cells were encapsulated in ABs, grown in hypoxic conditions for 7 days, and gene expression of the notochordal markers was evaluated. No combination was found to be significantly different from Brachyury alone. Thus we concluded that overexpression of Brachyury in PS cells and a 3D hypoxic environment is sufficient to induce iNC differentiation. Bars indicate SEs, $\#p<0.01$ when comparing to a sample not transfected with the same gene that is being tested, $*p<0.05$; $p<0.01$; $*p<0.001$; $****p<0.0001$.

In an attempt to improve the differentiation process by increasing specificity and/or efficiency, the step involving differentiation from PSs to iNCs was repeated with the addition of different combinations of plasmids encoding for Brachyury, Noto, and GDF6. By analysis of expression levels of characteristic notochordal genes, overexpression of Brachyury in PS cells and a 3D hypoxic environment appears to be sufficient to induce iNC differentiation (FIG. 15).

Example 22 iNC Gene Expression

Figure 16:
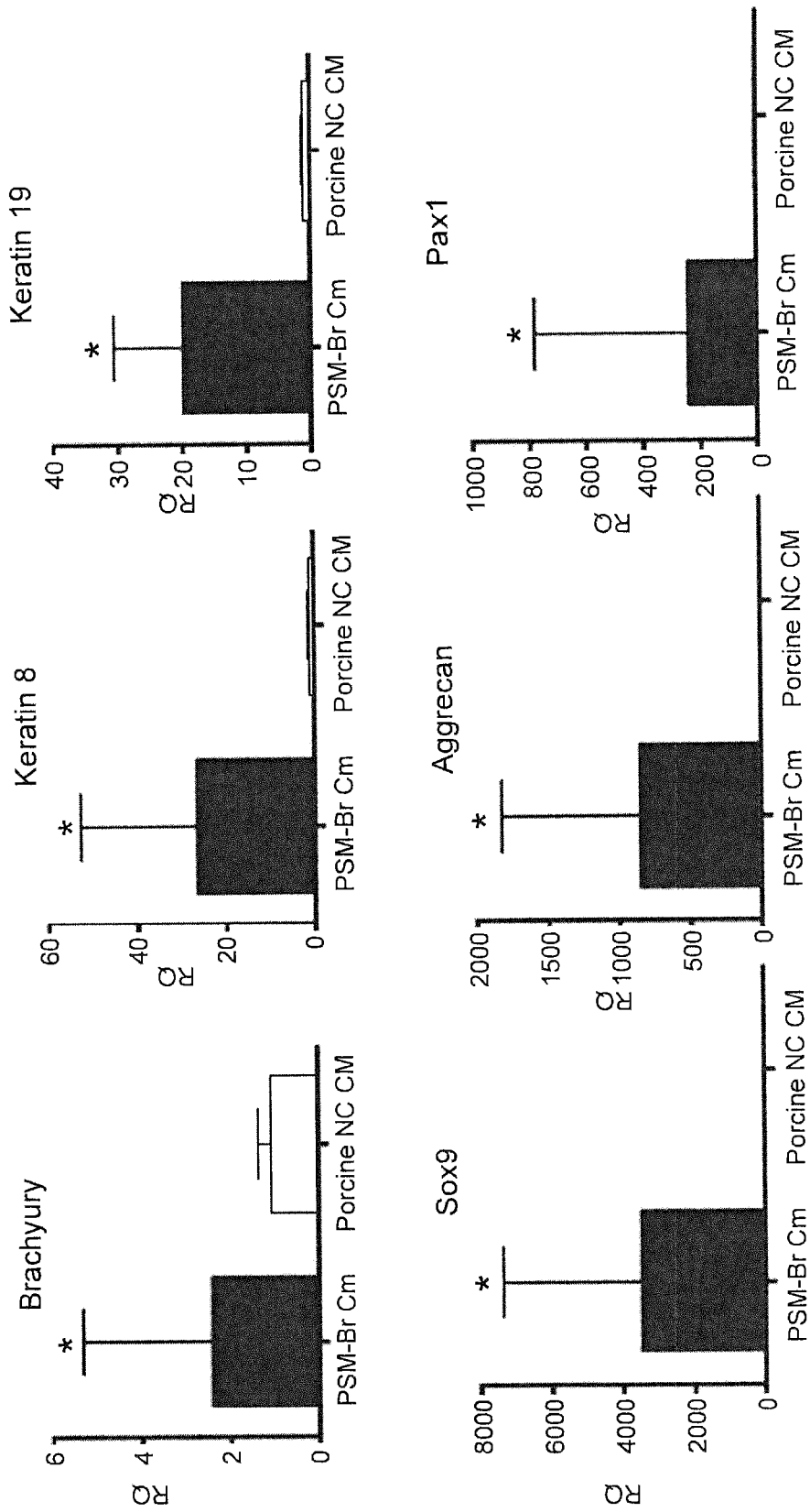
FIG. 16. iNC function: paracrine effect on BM-hMSCs. Notochordal conditioned medium (NCM) was collected from iNCs and porcine NCs grown in alginate beads, as reported. This medium was applied to BM-hMSCs encapsulated in alginate beads. Gene expression was evaluated on Day 7 and normalized to BM-hMSCs grown in control medium. iNC-NCM was found to induce significantly higher expression of NC and NP marker genes in BM-hMSCs than porcine NC-NCM. Bars indicate SEs, $*p<0.05$ FIG. 17. Porcine IVD model.

The Inventors then studied iNC gene expression and functionality in an in vitro microenvironment that resembles in vivo conditions. The cells were embedded in 3D Pura-Matrix® peptide hydrogel, (which has been successfully used in several cartilage repair and IVD cell therapymodels), following which the cells were stimulated by mechanical compression using the FlexCell® FX-5000 system (Flex-Cell Corp, Burlington, N.C.). The iNCs embedded in Pura-Matrix® peptide hydrogel sustained their viability and phenotype under NP differentiation conditions (FIG. 16). Furthermore, cell responses to mechanical loading in this setup have been intensively analyzed by the Inventors previous studies. Here, iNCs embedded in PuraMatrix® peptide hydrogel displayed downregulation of NP markers in response to compression strain, indicating the feasibility of a cell response to overloading in vitro.

Example 23

Co-Culture Studies

Following our protocol, iNCs were generated and tested in a co-culture system to assess the effect of these cells on NP cells, isolated from healthy porcine NPs. Both cell types were encapsulated in PuraMatrix® peptide hydrogel in a 1:1 ratio and cultured in NP differentiation conditions. Gene expression analysis showed that human cells expressed higher levels of Brachyury, Noggin, and Aggrecan, whereas porcine cells expressed higher levels of Sox9 and similar levels of Keratin 8 and Col2, indicating that there were more notochordal cells of human origin and more NP-like cells of porcine origin.

Example 24

Figure 18A:
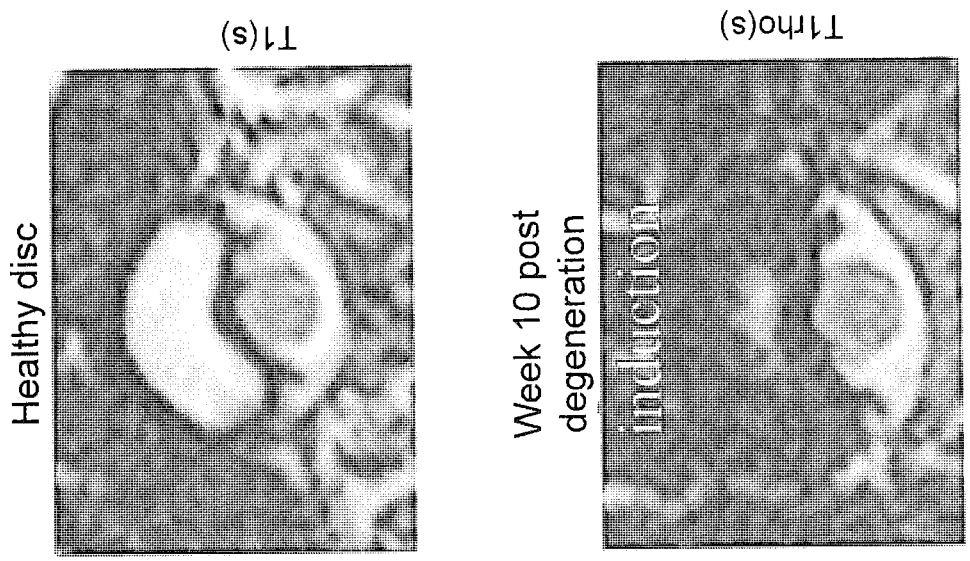
(FIG. 18A) A GAG phantom study demonstrating a linear relationship between the —OH CEST signal and GAG concentration.
Figure 18B:
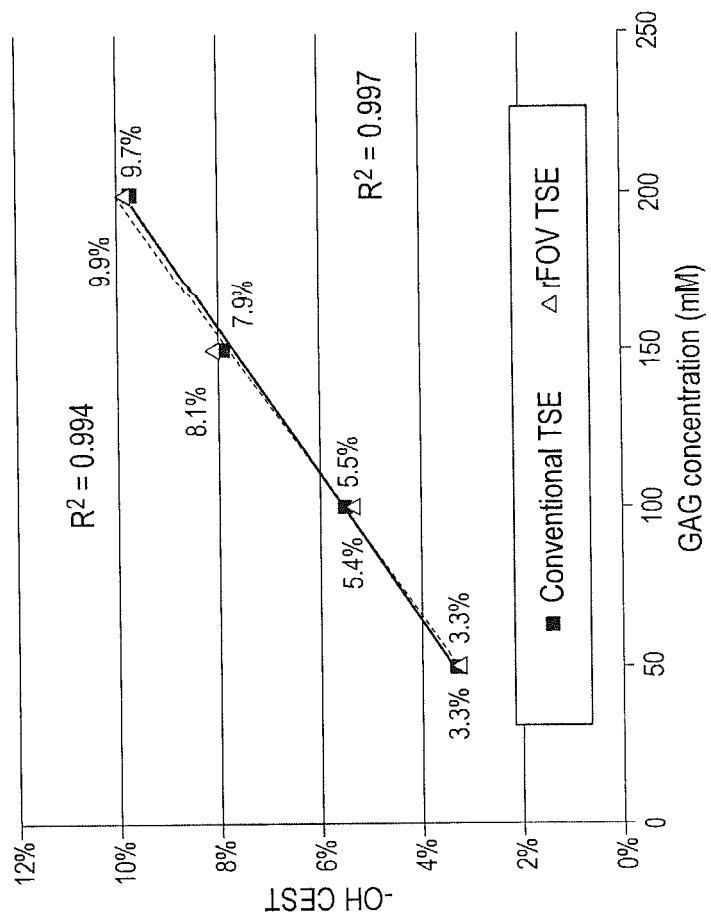
(FIG. 18B) Representative MRIs of healthy and degenerate porcine IVDs.
Figure 18C:
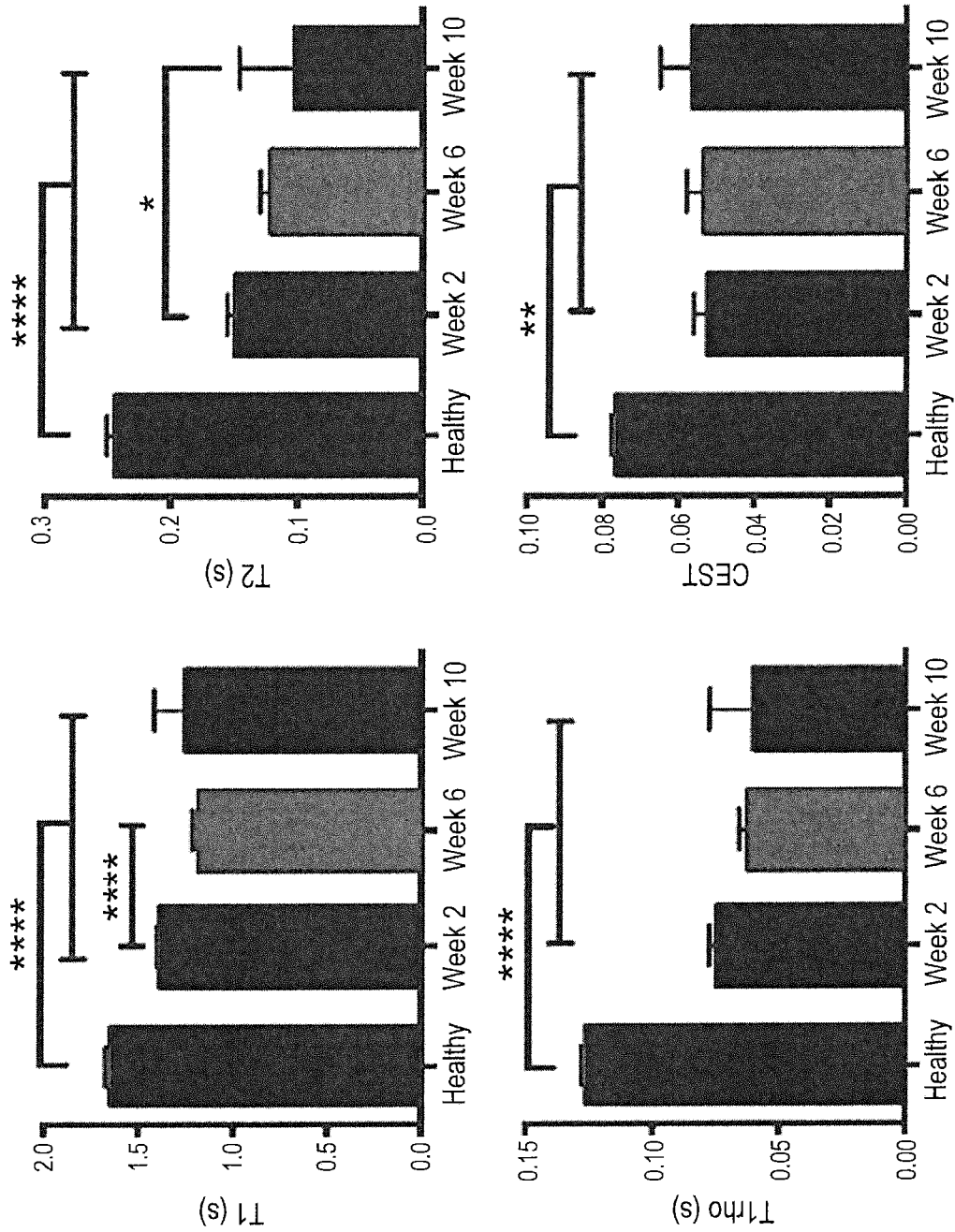
(FIG. 18C) Quantitation of MR imaging of IVDs after degeneration induction. There are significant decreases in T1, T2, Trho, and CEST values of the disc as early as 2 weeks post injury, indicating reductions in GAGs, collagens, and water content in the disc. Bars indicate SEs, $*p<0.05$; $p<0.01$; $**p<0.0001$.

Evaluation of the Regenerative Potential of iNCs in a Large Animal Model of IVD Degeneration This phase in the research is essential to assess to assess the engraftment, survival, and differentiation potential of human iNCs in a porcine model of disc degeneration in vivo. The Inventors have previously established a large animal model for disc degeneration that resembles in size the human IVD (FIGS. 17, 18). Not only are there implications of scaling with small versus large disc volume, but also some animals may be inappropriate just because the procedure proposed is physically challenging in small species. In small quadrupeds, such as rabbit, mouse, or rat, much lower forces are applied than in humans.

Figure 19:
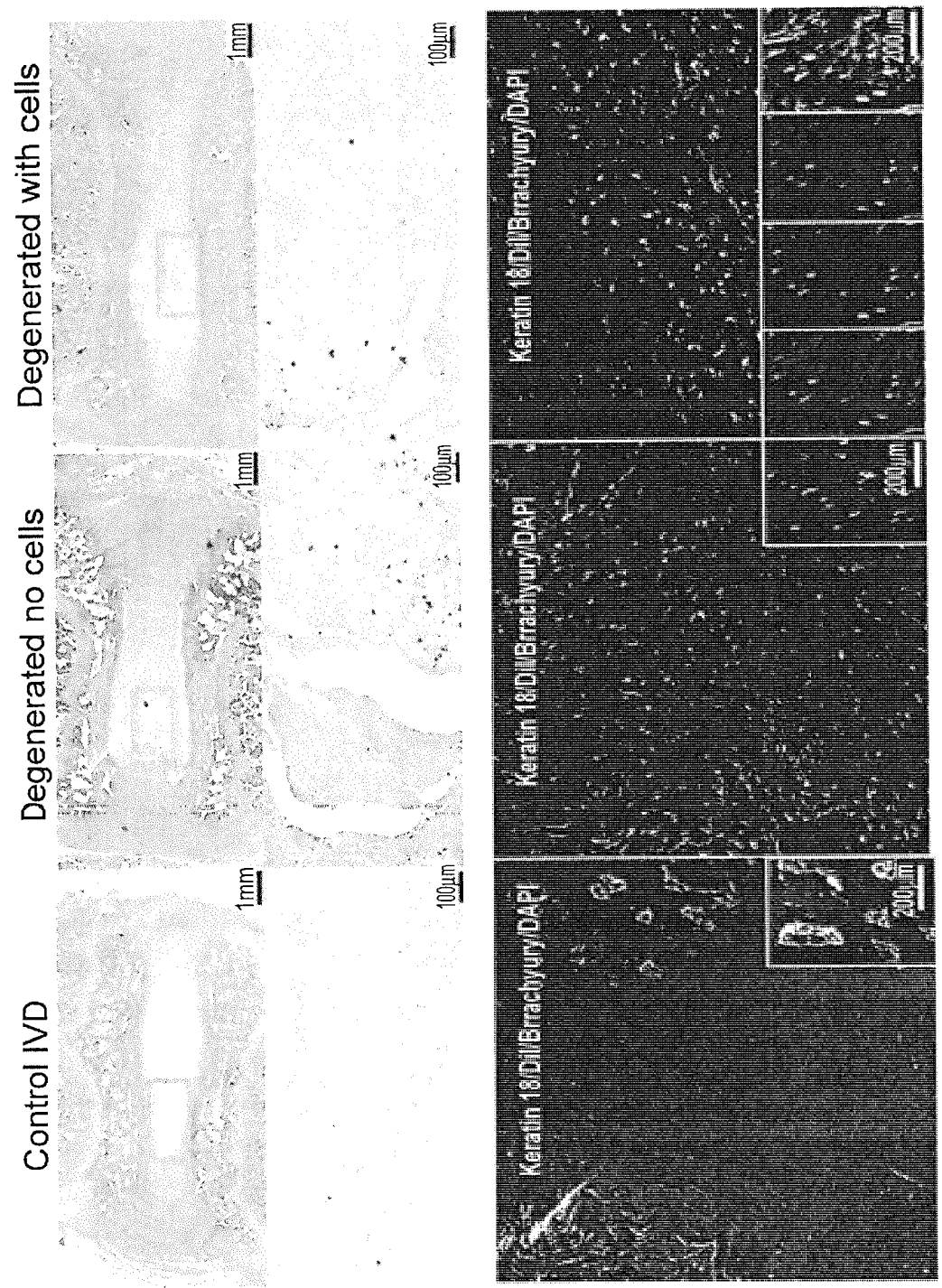
FIG. 19. iNC injection into degenerate porcine IVD: pilot study. 6 weeks after degeneration induction caused by annular puncture, DiI-labeled iNCs were injected into the NP. After 4 weeks, the IVDs were harvested, stained with H&E, and analyzed (FIG. 19A & FIG. 19B).

Biochemical composition of the disc differs between species, and IVDs in large quadrupeds more closely resemble discs in humans than those in small animals. Our previous study showed that annular injury—induced degeneration affects the phenotype of NP-residing cells, and thus we hypothesize that the addition of cells with the NC phenotype would rejuvenate the disc and activate resident cells for regeneration and repopulation of the disc. The IVD is an immunoprivileged organ that can be treated with xenogeneic human cells without risk of rejection. The Inventors previously showed the feasibility of iNC injection and survival of these cells in a degenerated IVD (FIG. 19). This pilot study showed that the cells could survive inside the degenerated IVD and keep their phenotype for at least 4 weeks (FIG. 19C). No cell infiltration or inflammation was observed in discs injected with human iNCs (FIGS. 19A & B).

Development of iNCs will provide a reproducible and inexhaustible source of human notochordal cells to treat DDD, which can be delivered in a minimally invasive manner to treat one cause of DDD, namely, exhaustion of the original NC population. If indeed we fully succeed, this proposed therapy could reverse the degeneration process and thereby significantly reduce the more than 650,000 spinal surgeries performed each year as well as alleviate the $50-$200 billion in annual hospital costs and questionable outcomes these surgeries represent.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods for preventing or treating intervertebral disease and related conditions, such as degenerative disc disease, methods of isolating or modifying notochordal cells used in the described techniques, compositions of therapeutic agents and/or noctochordal cells generated by the aforementioned techniques, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method for modulating intervertebral disc degeneration, comprising:
   culturing human induced pluripotent stem cells (iPSCs) in the presence of 4 μM, 5 μM or 6 μM of a glycogen synthase kinase 3 (GSK3i) inhibitor (GSK3i) for up to 6 days to form primitive streak (PS) cells;
   transfecting the PS cells with a vector encoding Brachyury to overexpress Brachyury;
   expressing Brachyury in the PS cells, wherein expression of Brachyury by the vector encoding Brachyury in the PS cells induces formation of human induced notochordal cells (iNCs) and the iNCs express Brachyury, Keratin 18, and Keratin 19; and
   administering a quantity of the iNCs into the nucleus pulposus tissue of a subject, wherein administration of human iNCs modulates intervertebral disc degeneration in the subject.

2. The method of claim 1, wherein the human iNCs are encapsulated in a hydrogel.

3. The method of claim 2, wherein the hydrogel comprises a peptide hydrogel.

4. The method of claim 2, wherein the hydrogel comprises fibrinogen hydrogel with an elasticity of 1 kPa.

5. The method of claim 1, wherein at least $1 \times 10^6$, $2 \times 10^6$, or $3 \times 10^6$ human iNCs are administered to the subject.

6. The method of claim 1, wherein modulating intervertebral disc degeneration comprises an increase in water content and/or disc height.

7. The method of claim 1, wherein culturing the human iPSCs to form PS cells comprises culturing in the presence of 5 μM of GSK3i.

8. The method of claim 1, wherein culturing the human iPSCs to form PS cells comprises culturing the iPSCs for 4 days.

9. The method of claim 1, wherein culturing the human iPSCs to form PS cells comprises culturing the iPSCs for 3 days.

* * * * *